US010835166B2

(12) United States Patent
Kurashima et al.

(10) Patent No.: US 10,835,166 B2
(45) Date of Patent: Nov. 17, 2020

(54) VIEWER EMOTION DETERMINATION APPARATUS THAT ELIMINATES INFLUENCE OF BRIGHTNESS, BREATHING, AND PULSE, VIEWER EMOTION DETERMINATION SYSTEM, AND PROGRAM

(71) Applicant: NATSUME RESEARCH INSTITUTE, CO., LTD., Tokyo (JP)

(72) Inventors: Wataru Kurashima, Tokyo (JP); Kouichi Kikuchi, Tokyo (JP)

(73) Assignee: Natsume Research Institute, Co., Ltd., Tokyo (JP)

(*) Notice: Subject to any disclaimer, the term of this patent is extended or adjusted under 35 U.S.C. 154(b) by 260 days.

(21) Appl. No.: 15/764,330

(22) PCT Filed: Sep. 29, 2016

(86) PCT No.: PCT/JP2016/078917
§ 371 (c)(1),
(2) Date: Mar. 29, 2018

(87) PCT Pub. No.: WO2017/057631
PCT Pub. Date: Apr. 6, 2017

(65) Prior Publication Data
US 2018/0296088 A1 Oct. 18, 2018

(30) Foreign Application Priority Data

Oct. 1, 2015 (JP) .................................. 2015-195572
Apr. 1, 2016 (JP) .................................. 2016-074014

(51) Int. Cl.
G06K 9/00 (2006.01)
A61B 5/16 (2006.01)
(Continued)

(52) U.S. Cl.
CPC .............. *A61B 5/163* (2017.08); *A61B 3/112* (2013.01); *A61B 5/0816* (2013.01); *A61B 5/165* (2013.01);
(Continued)

(58) Field of Classification Search
CPC ........... A61B 3/11; A61B 3/112; A61B 5/165; A61B 3/113; A61B 5/7203; A61B 5/163;
(Continued)

(56) References Cited

U.S. PATENT DOCUMENTS 6,090,051 A * 7/2000 Marshall ................ A61B 5/163
600/558
2015/0077543 A1 * 3/2015 Kerr ...................... H04N 5/2256
348/135

FOREIGN PATENT DOCUMENTS

JP 2009-201653 A 9/2009
JP WO2011/042989 A1 4/2011
(Continued)

OTHER PUBLICATIONS

International Search Report of International Application No. PCT/JP2016/078917 completed Nov. 16, 2016 and dated Nov. 29, 2016 (2 pages).

*Primary Examiner* — Christine H Matthews
*Assistant Examiner* — Joshua Daryl D Lannu
(74) *Attorney, Agent, or Firm* — Pyprus Pte Ltd

(57) ABSTRACT

To determine the emotion of a viewer more accurately by measuring the pupil diameter while eliminating the influence of brightness, breathing, and pulse. A reference data measuring unit measures, as reference data, a reference pupil diameter Csk, a breathing influenced pupil diameter Dskt, and a pulse influenced pupil diameter Eskt for each of various combinations of the brightness of an entire screen and the brightness of a visual point. A measuring unit identifies the reference pupil diameter Csk, the breathing influenced pupil diameter Dskt, and the pulse influenced pupil diameter Eskt corresponding to the elapsed time of
(Continued)

content. The measuring unit sets a pupil diameter Bt as an attentive pupil diameter A1t in the case of two or more breathing times (T1), calculates the attentive pupil diameter A1t by subtracting the breathing pupil diameter Dskt from the pupil diameter Bt in the case of two or more pulse times and less than two breathing times (T2), and calculates the attentive pupil diameter A1t by further subtracting the pulse influenced pupil diameter Eskt therefrom in the case of less than two pulse times (T3). The measuring unit calculates an attention-attributable pupil diameter A2t by subtracting the reference pupil diameter Csk from the attentive pupil diameter A1t, and divides the attentive pupil diameter A1t and the attention-attributable pupil diameter A2t by the reference pupil diameter Csk to calculate the degrees of attention P1t and P2t.

7 Claims, 20 Drawing Sheets

(51) Int. Cl.
*A61B 5/08* (2006.01)
*A61B 5/00* (2006.01)
*A61B 3/11* (2006.01)
*A61B 5/02* (2006.01)
*A61B 3/113* (2006.01)

(52) U.S. Cl.
CPC ........ *A61B 5/7203* (2013.01); *G06K 9/00597* (2013.01); *A61B 3/11* (2013.01); *A61B 3/113* (2013.01); *A61B 5/0059* (2013.01); *A61B 5/02* (2013.01)

(58) Field of Classification Search
CPC ....... A61B 5/0059; A61B 5/0816; A61B 5/02; G06K 9/00597
See application file for complete search history.

(56) References Cited

FOREIGN PATENT DOCUMENTS

| | | |
|---|---|---|
| JP | 5445981 B2 | 1/2014 |
| JP | WO2015/056742 A1 | 4/2015 |

* cited by examiner

| REFERENCE PUPIL DIAMETER Csk (mm) | BRIGHTNESS OF VISUAL POINT (s) | | | | |
|---|---|---|---|---|---|
| | 0%(1) | 25%(2) | 50%(3) | 75%(4) | 100%(5) |
| BRIGHTNESS OF ENTIRE SCREEN (k)  0%(1) | | | | | |
| 25%(2) | | | | | |
| 50%(3) | | | | | |
| 75%(4) | | | | | |
| 100%(5) | | | | | |

60      REFERENCE BRIGHTNESS/DARKNESS RESPONSE TABLE

61 REFERENCE RESPIRATION RESPONSE TABLE

PUPIL DIAMETER Bt BASED ON REFERENCE
BRIGHTNESS/DARKNESS SCREEN

PUPIL DIAMETER/EXCLUDING INFLUENCE OF PULSE AND INCLUDING INFLUENCE OF
RESPIRATION BASED ON REFERENCE BRIGHTNESS/DARKNESS SCREEN
(MOVING AVERAGE OVER TWO PULSE TIMES OR MORE AND LESS THAN TWO
RESPIRATION TIMES)

INFLUENCE OF RESPIRATION ON PUPIL DIAMETER

Fig. 19

| D11 | D21 | D31 | · · | DK1 |
|-----|-----|-----|-----|-----|
| D12 | D22 | D32 | · · | DK2 |
| D13 | D23 | D33 | · · | DK3 |
| · · | · · | · · | · · | · · |
| D1L | D2L | D3L | · · | DKL |

DIVISION EXAMPLE OF DISPLAY SCREEN

Fig. 20

(a, b) ┌──────────────────────────────────────┐ (c, b)
       │   HOW DO YOU THINK ABOUT PRODUCT DESIGN │
       │     THAT YOU HAVE PREVIOUSLY VIEWED?    │
       │               (d, e)                    │
(a, e) ├──────────────────┬──────────────────────┤ (c, e)
       │                  │                      │
       │  A I DON'T THINK IT'S GOOD │ B I THINK IT'S GOOD │
       │                  │                      │
       └──────────────────┴──────────────────────┘
(a, f)              (d, f)                    (c, f)

SCREEN EXAMPLE OF TWO-CHOICE QUESTIONNAIRE

SCREEN EXAMPLE OF RESULT OF TWO-CHOICE QUESTIONNAIRE

| (a, b) | (d, e) | (c, b) |
|---|---|---|
| (a, e) | | (c, e) |
| A  I DON'T THINK IT'S GOOD | B  IT'S QUITE GOOD | |
| (a, f) | (d, f) | (c, f) |
| C  IT'S NOT QUITE GOOD | D  I THINK IT'S GOOD | |
| (a, g) | (d, g) | (c, g) |

HOW DO YOU THINK ABOUT PRODUCT DESIGN THAT YOU HAVE PREVIOUSLY VIEWED?

SCREEN EXAMPLE OF FOUR-CHOICE QUESTIONNAIRE

SCREEN EXAMPLE OF RESULT OF FOUR-CHOICE QUESTIONNAIRE

VIEWER EMOTION DETERMINATION APPARATUS THAT ELIMINATES INFLUENCE OF BRIGHTNESS, BREATHING, AND PULSE, VIEWER EMOTION DETERMINATION SYSTEM, AND PROGRAM

TECHNICAL FIELD

The present invention relates to a viewer's feeling determination device, a viewer's feeling determination system, and a program which utilize that a pupil diameter expands when a viewer pays attention to a visual object, and to a technique for excluding influence of brightness/darkness of the visual object and respiration and pulse of the viewer when measuring a pupil diameter of the viewer with respect to the visual object.

BACKGROUND ART

Conventionally, as a technique for determining where a person is looking at, a visual-point position is measured, a stay time of the visual point toward the visual object is calculated, and an attention degree toward the visual object is measured. In such a method, when the stay time of the visual point is long although the viewer is just vaguely looking at a visual object, it is erroneously determined that the attention degree toward the visual object is high. In addition, the stay of the visual point can be measured for a still image, but is hardly measured for a moving image.

In order to solve such a problem, there is a known technique for determining a level of an attention degree toward a visual object simultaneously utilizing a phenomenon in which a pupil diameter expands when a person pays attention to a visual object (see, for example, Patent Literatures 1 and 2).

In the techniques of Patent Literatures 1 and 2, movement of an eyeball is imaged, the movement of gaze, the pupil diameter, and the like are measured to measure the attention degree toward the visual object. Specifically, a relationship between luminance of a display and a pupil diameter is measured in advance regarding a brightness/darkness response to content for each viewer. Then, the luminance of the display at the time of viewing actual content is measured, and a pupil diameter caused only by the brightness/darkness response corresponding to the luminance is subtracted from the actually-measured pupil diameter referring to the relationship between the luminance and the pupil diameter measured in advance. As a result, it is possible to accurately measure the pupil diameter of the viewer corresponding to the attention toward the content displayed on the display.

CITATION LIST

Patent Literature

Patent Literature 1: Japanese Patent No. 5445981
Patent Literature 2: WO 2015/056742 A

SUMMARY OF INVENTION

Technical Problem

Meanwhile, similarly to the attention degree, there is a phenomenon in which the pupil diameter contracts in a bright place and expands in a dark place, but there is a difference between individuals. In order to solve this individual difference, a brightness/darkness screen as a reference (reference brightness/darkness screen) is used to define a level of the attention degree based on a ratio obtained using a difference between a pupil diameter when viewing the darkest screen and a pupil diameter when viewing the brightest screen as a denominator, and a difference between a pupil diameter when viewing an actual visual object and a pupil diameter when viewing the reference brightness/darkness screen having the same luminance condition as the actual visual object (a pupil diameter corresponding to attention) as a numerator.

In this case, there is a case where a pupil diameter corresponding to attention in a dark screen is different from a pupil diameter corresponding to attention in a bright screen even for the same magnitude of attention in the calculation of the numerator defining the level of the attention degree. Thus, there is a case where the attention degree is not correctly expressed so that there is a request for a method of expressing a correct attention degree common to brightness/darkness. In addition, when the viewer is bored at viewing the visual object, a numerical value of the attention degree may become negative (−) in some cases, and it is difficult to directly use this numerical value in calculation of an application. Thus, it is necessary to handle the numerical value of the attention degree as a positive number.

Further, the pupil diameter periodically changes depending on respiration and pulse. Thus, in order to more accurately measure the attention degree toward the visual object, it is desired to exclude influence of brightness/darkness of the visual object and the respiration and pulse of the viewer at the time of measuring the pupil diameter.

Therefore, the present invention has been made to solve the above problems, and an object thereof is to provide a viewer's feeling determination device, a viewer's feeling determination system, and a program capable of measuring a pupil diameter excluding influence of brightness/darkness, respiration, and pulse, and more accurately measuring a viewer's feeling.

Solution to Problem

A first aspect of the present invention relates to a viewer's feeling determination device. This viewer's feeling determination device is a viewer's feeling determination device that determines a feeling of a viewer based on a pupil diameter of the viewer who views content displayed on a display. Then, the viewer's feeling determination device includes a memory unit and a measurement unit.

When a predetermined reference brightness/darkness screen is displayed on a first screen and brightness of the first screen and brightness of a visual-point position when a visual point of the viewer is aligned to a predetermined position on the first screen are changed, the memory unit stores reference data relating to a pupil diameter of the viewer based on a pupil diameter of the viewer measured for each of combinations of the brightness of the first screen and the brightness of the visual-point position in the reference brightness/darkness screen.

A measurement unit measures a pupil diameter of the viewer when the content is displayed on the display to obtain an actually-measured pupil diameter, specifies the reference data corresponding to brightness of the display on which the content is displayed and brightness of a visual-point position in the display on which the content is displayed based on the reference data stored in the memory unit, and corrects the actually-measured pupil diameter based on the actually-measured pupil diameter and the specified reference data to obtain a corrected pupil diameter.

In a preferable example of the above-described viewer's feeling determination device, the reference data is measured by a reference data measurement unit.

Further, the reference data measurement unit includes a reference brightness/darkness response measuring unit that sets a predetermined time interval of two respiration times or more with a respiration cycle of the viewer as one respiration time, moving-averages the pupil diameter over the time interval to obtain a moving-averaged pupil diameter for each of the combinations of the brightness of the first screen and the brightness of the visual-point position in the reference brightness/darkness screen, averages the moving-averaged pupil diameter based on a time for which the reference brightness/darkness screen is displayed to obtain a reference pupil diameter, and generates a reference brightness/darkness response table including the reference pupil diameter for each of the combinations of the brightness of the first screen and the brightness of the visual-point position in the reference brightness/darkness screen.

In addition, the measurement unit includes: a reference pupil diameter and others specifying unit that specifies the reference pupil diameter, which corresponds to the brightness of the display on which the content is displayed and the brightness of the visual-point position in the display on which the content is displayed, based on the reference brightness/darkness response table generated by the reference brightness/darkness response measuring unit; and a unit that sets a predetermined time interval equal of the two respiration times or more, moving-averages the pupil diameter over the time interval to obtain a moving-averaged pupil diameter and define the moving-averaged pupil diameter as an attention pupil diameter, and subtracts the reference pupil diameter specified by the reference pupil diameter and others specifying unit from the moving-averaged pupil diameter to obtain a pupil diameter corresponding to attention.

A preferable example of the above-described viewer's feeling determination device includes an analysis unit that measures respiration state data including timings of an inhalation start point and an exhalation start point in the viewer's respiration. The reference data measurement unit further includes a reference respiration response measuring unit that sets a predetermined time interval of two pulse times or more and less than two respiration times with the respiration cycle of the viewer as one respiration time and a pulse cycle of the viewer as one pulse time, moving-averages the pupil diameter over the time interval for each of the combinations of the brightness of the first screen and the brightness of the visual-point position in the reference brightness/darkness screen to obtain a moving-averaged pupil diameter, averages the moving-averaged pupil diameter based on a time for which the reference brightness/darkness screen is displayed to obtain an average value, subtracts the average value from the moving-averaged pupil diameter to obtain a pupil diameter influenced only by the respiration as a subtraction result, and extracts a respiration pupil diameter in a time of one respiration cycle including the inhalation start point and the exhalation start point from a temporal change of the pupil diameter influenced only by the respiration using the respiration state data measured by the analysis unit to generate a reference respiration response table formed of the respiration pupil diameter for each of the combinations of the brightness of the first screen and the brightness of the visual-point position in the reference brightness/darkness screen. The reference pupil diameter and others specifying unit of the measurement unit specifies the reference pupil diameter and further specifies the respiration pupil diameter corresponding to the brightness of the display on which the content is displayed and the brightness of the visual-point position in the display on which the content is displayed based on the reference respiration response table generated by the reference brightness/darkness response measuring unit. The attention pupil diameter and others calculating unit of the measurement unit sets the predetermined time interval of two pulse times or more and less than two respiration times, moving-averages the pupil diameter over the time interval to obtain a moving-averaged pupil diameter, subtracts the respiration pupil diameter specified by the reference pupil diameter and others specifying unit from the moving-averaged pupil diameter to obtain an attention pupil diameter, and further subtracts the reference pupil diameter specified by the reference pupil diameter and others specifying unit from a result of the subtraction to obtain a pupil diameter corresponding to attention.

In a preferable example of the above-described viewer's feeling determination device, the analysis unit measures pulse state data including a timing of a pulse start point in the viewer's pulse in addition to the respiration state data. The reference data measurement unit further includes a reference pulse response measuring unit that sets a predetermined time interval of two pulse times or more and less than two respiration times with the respiration cycle of the viewer as one respiration time and the pulse cycle of the viewer as one pulse time, moving-averages the pupil diameter over the time interval to obtain a moving-averaged pupil diameter, subtracts the moving-averaged pupil diameter from the pupil diameter to obtain a pupil diameter influenced only by the pulse as a subtraction result, and extracts a pulse pupil diameter in a time of one pulse cycle including the pulse start point from a temporal change of the pupil diameter influenced only by the pulse using the pulse state data measured by the analysis unit to generate a reference pulse response table formed of the pulse pupil diameter for each of the combinations of the brightness of the first screen and the brightness of the visual-point position in the reference brightness/darkness screen. The reference pupil diameter and others specifying unit of the measurement unit specifies the reference pupil diameter and the respiration pupil diameter and further specifies the pulse pupil diameter corresponding to the brightness of the display on which the content is displayed and the brightness of the visual-point position in the display on which the content is displayed based on the reference pulse response table generated by the reference brightness/darkness response measuring unit. The attention pupil diameter and others calculating unit of the measurement unit subtracts the pulse pupil diameter and the respiration pupil diameter specified by the reference pupil diameter and others specifying unit from the pupil diameter to obtain an attention pupil diameter, and further subtracts the reference pupil diameter specified by the reference pupil diameter and others specifying unit from a result of the subtraction to obtain a pupil diameter corresponding to attention.

In a preferable example of the above-described viewer's feeling determination device, the measurement unit further includes an attention degree calculating unit that calculates a ratio between the reference pupil diameter specified by the reference pupil diameter and others specifying unit and the attention pupil diameter obtained by the attention pupil diameter and others calculating unit to obtain a first attention degree, and calculates a ratio between the reference pupil diameter specified by the reference pupil diameter and others specifying unit and the pupil diameter corresponding to attention obtained by the attention pupil diameter and others calculating unit to obtain a second attention degree.

In a preferable example of the above-described viewer's feeling determination device, when a plurality of division areas obtained by dividing a screen of the display are set and there are a plurality of the viewers, the measurement unit obtains an attention degree per the single viewer with respect to the content by obtaining the first attention degree with respect to the content displayed on the display as a first content attention degree for each of the plurality of viewers, summing the first content attention degrees for the plurality of viewers to obtain a first total result, and dividing the first total result by a number the viewers, obtains a distribution of attention degrees for each of the division areas with respect to the content by obtaining the first attention degree for each of the division areas as a first area attention degree for each of the plurality of viewers, summing the first area attention degrees for the plurality of viewers to obtain a second total result, and dividing the second total result by the first total result, and obtains a distribution of attention degrees for each of the division areas per unit time with respect to the content by integrating the distribution of attention degrees for each of the division areas with respect to the content based on a predetermined time period to obtain a total distribution of attention degrees for each of the division areas, and dividing the total distribution of the attention degrees for each of the division areas by the predetermined time period.

In a preferable example of the viewer's feeling determination device, when a screen of a questionnaire including a question field and a plurality of answer fields is displayed on the display, the measurement unit obtains each field attention degree for each of the question fields and the plurality of answer fields by integrating the first attention degree for each of the question fields and the plurality of answer fields based on a predetermined time period, obtains a first total result by summing the field attention degrees, respectively, for the question field and the plurality of answer fields and obtains a second total result by summing the field attention degrees, respectively, for the plurality of answer fields, obtains an answering confidence ratio for each of the plurality of answer fields by dividing each of the field attention degrees for each of the plurality of answer fields by the second total result, and obtains a level of an attention degree for the questionnaire by dividing the first total result by the predetermined time period.

In a preferable example of the viewer's feeling determination device, the pupil diameter of the viewer, which is obtained based on the reference data, is measured after one second or more or one minute or less for each change of a predetermined reference brightness/darkness screen of the first screen, after a lapse of 40 seconds or more or ten minutes or less since the predetermined reference brightness/darkness screen of the first screen is first displayed for the viewer.

When the pupil diameter was measured a plurality of times while shifting time under the same conditions, a pupil diameter measured immediately after brightening the screen and a pupil diameter measured after a lapse of a long time from then had a large value of a variance (and hence a standard deviation) and there were variations. Thus, values of a pupil diameter measured immediately after the above-described variation and a pupil diameter measured after a lapse of a long time from then have a lower stability (and hence reliability) than the pupil diameter measured in a predetermined period. Accordingly, it is preferable to measure the pupil diameter after a lapse of several seconds or more from the change of the brightness of the screen. In addition, when the pupil diameter is measured each time the brightness of the reference brightness/darkness screen of the first screen is changed, after a lapse of one second or more and one minute or less (preferably one second or more and ten seconds or less, two seconds or more and seven seconds or less, or three seconds or more and six seconds or less) from the change, the variation in the pupil diameter is reduced, which is preferable.

A second aspect of the present invention relates to a viewer's feeling determination system. This viewer's feeling determination system includes: a viewer's feeling determination device that determines a feeling of a viewer based on a pupil diameter of the viewer who views an object; a brightness measurement device that measures brightness of an entire visual image including the object viewed by the viewer and brightness of a visual-point position of the viewer inside the object; and a visible image capturing device that captures the visual image. The viewer's feeling determining device includes: a reference data measurement unit that measures reference data relating to the pupil diameter of the viewer, when brightness of a predetermined reference image including the object and brightness of the visual-point position when a visual point of the viewer is aligned to a predetermined position inside the reference image are changed, based on the pupil diameter for each of combinations of the brightness of the reference image and the brightness of the visual-point position; and a measurement unit that specifies the reference data for each of combinations of brightness of an entire reference image measured by the reference data measurement unit and the brightness of the visual-point position when the viewer views the object, and measures a new pupil diameter based on the pupil diameter and the reference data. The brightness measurement device includes: an imaging unit in which a plurality of luminance sensors are arranged to correspond to the entire visible image; and a visual-point position luminance measurement unit that specifies a luminance sensor corresponding to the visual-point position when the viewer views the object among the plurality of luminance sensors by using a table in which a relationship between the plurality of luminance sensors and the visual-point position is defined, and outputs luminance measured by the luminance sensor as the brightness of the visual-point position of the viewer.

A third aspect of the present invention relates to a program. This program is a program for determining a feeling of a viewer based on a pupil diameter of the viewer who views content displayed on a display. Further, this program causes a computer to execute: a step of reading reference data relating to the pupil diameter of the viewer, when a predetermined reference brightness/darkness screen is displayed on a first screen and brightness of the first screen and brightness of a visual-point position when a visual point of the viewer is aligned to a predetermined position on the first screen are changed a plurality of times, from a memory unit based on a pupil diameter of the viewer measured for each of combinations of the brightness of the first screen and the brightness of the visual-point position in the reference brightness/darkness screen; a step of specifying the reference data corresponding to brightness of the display on which the content is displayed and brightness of a visual-point position in the display on which the content is displayed based on the reference data when the content is displayed on the display; and a step of a corrected pupil diameter by receiving information on an actually-measured pupil diameter at the time of measuring the pupil diameter of the viewer when the content is displayed on the display and correcting the actually-measured pupil diameter based on the actually-measured pupil diameter and the specified reference data.

Advantageous Effects of Invention

As described above, it is possible to measure the pupil diameter excluding the influence of brightness/darkness, respiration, and pulse, and to more accurately determine the viewer's feeling according to the present invention.

BRIEF DESCRIPTION OF DRAWINGS

FIG. 19 is a view illustrating an example in which a screen of a display is divided.

FIG. 20 is a view illustrating a screen example of a two-choice questionnaire.

FIG. 29 is a view for describing a visual-point position St and the like inside a visual image a.

DESCRIPTION OF EMBODIMENTS

Hereinafter, modes for carrying out the present invention will be described in detail with reference to the drawings. The present invention is characterized by measuring a pupil diameter corresponding only to an attention degree by measuring a pupil diameter responsive to brightness/darkness, respiration, and pulse in advance as reference data and correcting a pupil diameter at the time of actually viewing an object using the reference data. As a result, it is possible to measure the pupil diameter excluding influence of brightness/darkness, respiration, and pulse, and to more accurately determine a viewer's feeling.

[Viewer Feeling Determination System and Example of Viewing Content Displayed on Display]

First, a viewer's feeling determination system including a viewer's feeling determination device according to an embodiment of the present invention will be described. In this example, when a viewer views content displayed on a display, a pupil diameter excluding the influence of brightness/darkness, respiration and pulse is measured, the attention degree is calculated, and a feeling of the viewer is determined.

Figure 1:
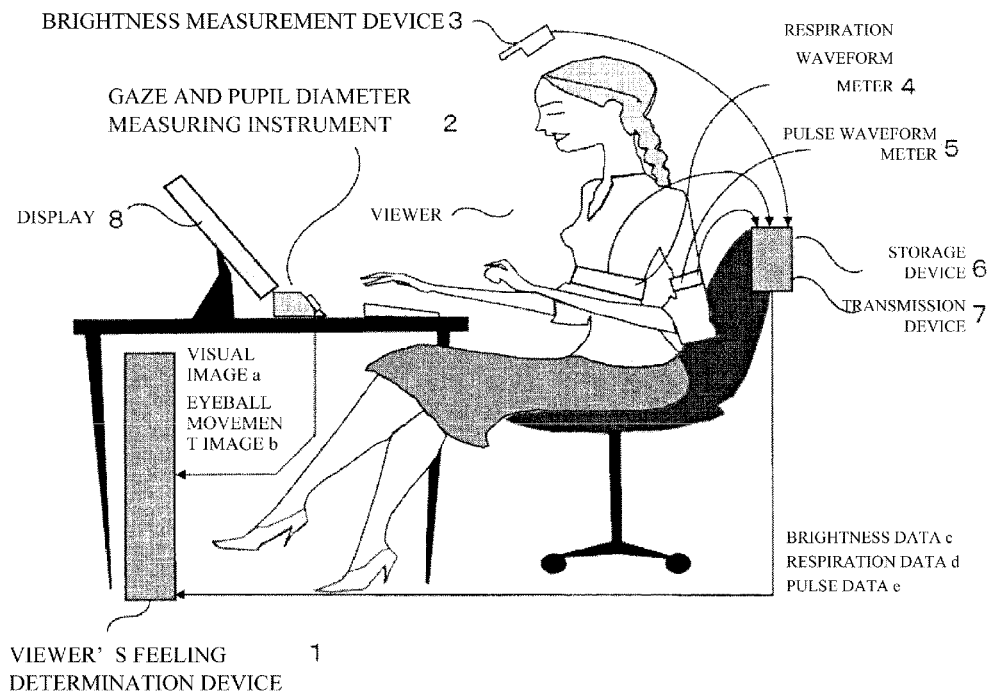
FIG. 1 is a schematic view illustrating a configuration example of a viewer's feeling determination system including a viewer's feeling determination device according to an embodiment of the present invention.

FIG. 1 is a schematic view illustrating a configuration example of the viewer's feeling determination system including the viewer's feeling determination device according to the embodiment of the present invention. The viewer's feeling determination system is configured to include a viewer's feeling determination device 1, a gaze and pupil diameter measuring instrument 2, a brightness measurement device 3, a respiration waveform meter 4, a pulse waveform meter 5, a storage device 6, a transmission device 7, and a display 8.

A first screen and the display (second screen) may be the same display device. In the case where the first screen and the display are the same display device, accuracy becomes higher since luminances of these display devices coincide with each other, so that the accuracy becomes higher. Meanwhile, the present invention is also used for an application of measuring reference data at a certain place and measuring the feeling at a viewer's workplace or at home. Then, the present invention can be used for an application of notifying a break signal, for example, when exhibiting a feeling that work efficiency is lowered in the workplace. In addition, for example, it is possible to notify a patient with depression of medication only when the medication is required so that it is possible to prevent severe depression. In this case, the first screen and the display (second screen) may be different display devices. In the following description, however, an example in which the first screen and the display (second screen) are the same display device will be described for simplicity.

Next, when obtaining the reference data, brightness of the entire first screen may be grasped, and the reference data may be obtained on the basis thereof. On the other hand, when the first screen partially emits light, brightness of this part may be grasped, and reference data may be created on the basis thereof.

When changing the brightness of the first screen, the way of changing the brightness may be in stages (gradually brightening or gradually darkening the first screen), or the brightness may be changed randomly or with certain rules. For example, when the brightness is changed to five levels from 0 to 5, it may be changed as 0→4→1→5→3→2. In addition, the brightness may be changed as 0→4→1→5→3→2→4 such that the same brightness is obtained a plurality of times to obtain a variation between pupil diameters at the same brightness and use the obtained variation as one of indicators for data reliability.

Incidentally, the viewer's feeling determination device of the present invention may store the reference data in advance, read the stored reference data when measuring the pupil diameter of the viewer to be used for correction of the actually-measured pupil diameter, and determine the viewer's feeling based on the corrected pupil diameter and the like. In this case, a memory unit that stores the reference data may be included in the viewer's feeling determination device or present outside the viewer's feeling determination device. The viewer's feeling determination device of the present invention may be realized as a wearable device. In this case, the wearable device is preferably configured to be capable of exchanging information with a computer that includes a display as an output device. Hereinafter, a description will be given on the basis of the viewer's feeling determination device of the present invention including a reference data measurement unit.

The viewer's feeling determination device 1 receives a visual image a and an eyeball movement image b from the gaze and pupil diameter measuring instrument 2 to be described later using a predetermined communication method, and further, receives brightness data c, respiration data d and pulse data e from the transmission device 7 using a predetermined communication method.

The viewer's feeling determination device 1 measures the pupil diameter responsive to the brightness/darkness, respiration, and pulse in advance as the reference data in a state where a reference brightness/darkness screen is displayed on the display 8. Then, the viewer's feeling determination device 1 measures the pupil diameter of the viewer with content displayed on the display 8 as an object and correcting the pupil diameter using the reference data, thereby calculating an attention pupil diameter, a pupil diameter corresponding to attention, and an attention degree. Then, the viewer's feeling determination device 1 determines the viewer's feeling based on the attention degree or objectively evaluates the content by performing statistical processing on a plurality of viewers. Details of the viewer's feeling determination device 1 will be described later.

The gaze and pupil diameter measuring instrument 2 acquires the visual image a of the content captured by a camera (not illustrated) when the viewer is viewing the content displayed on the display 8, and the eyeball movement image b captured by a camera (not illustrated) which is an image of the eyeball of the viewer to measure a visual-point position of the viewer and the pupil diameter. Then, the gaze and pupil diameter measuring instrument 2 transmits the visual image a and the eyeball movement image b to the viewer's feeling determination device 1 using a predetermined communication method.

The brightness measurement device 3 has a function of measuring brightness data indicating brightness of an object viewed by the viewer. In this example, the brightness measurement device 3 measures luminance of the entire screen of the display 8 and luminance of a predetermined position inside the screen. The respiration waveform meter 4 has a function of measuring a waveform relating to the viewer's respiration (respiration data). The respiration data includes data indicating timings of a start of exhalation and a start of inhalation regarding the respiration. The pulse waveform meter 5 has a function of measuring a waveform relating to the viewer's pulse (pulse data). The pulse data includes data indicating a timing of a start of pulse.

Each of the brightness data from the brightness measurement device 3, the respiration data from the respiration waveform meter 4, and the pulse data from the pulse waveform meter 5 is input to and stored in the storage device 6. The transmission device 7 transmits the various types of data stored by the storage device 6 to the viewer's feeling determination device 1, as the synchronized brightness data c, respiration data d, and pulse data e, using a predetermined communication method.

On the display 8, the reference brightness/darkness screen is displayed at the time of measurement of the reference data, and predetermined content is displayed at the time of determining the viewer's feeling.

[Viewer's Feeling Determination Device]

Figure 2:
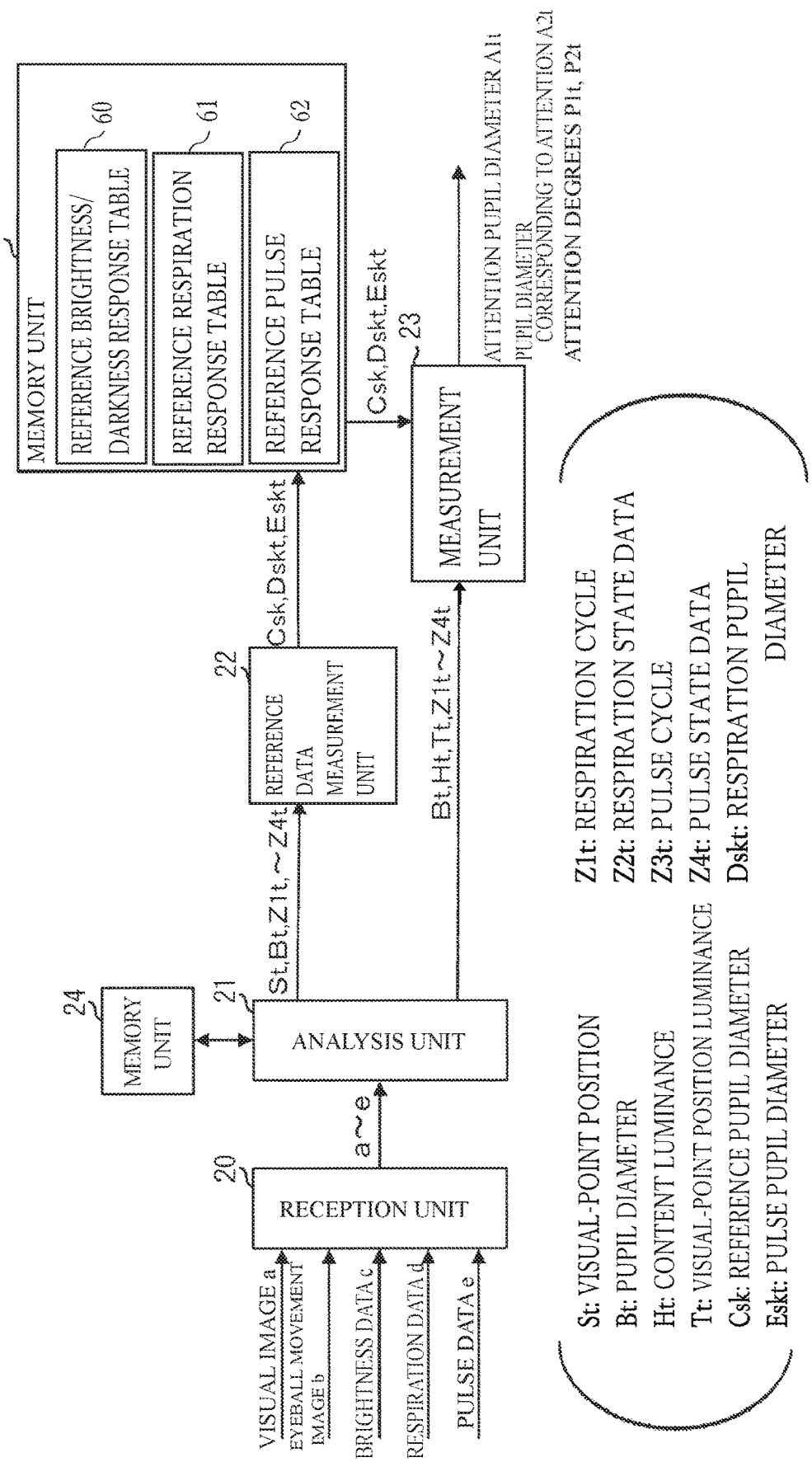
FIG. 2 is a block diagram illustrating a configuration example of the viewer's feeling determination device according to the embodiment of the present invention.

Next, the viewer's feeling determination device 1 illustrated in FIG. 1 will be described in detail. FIG. 2 is a block diagram illustrating a configuration example of the viewer's feeling determination device 1 according to the embodiment of the present invention. The viewer's feeling determination device 1 includes a reception unit 20, an analysis unit 21, a reference data measurement unit 22, a measurement unit 23, and memory units 24 and 25.

The viewer's feeling determination device 1 measures the reference data relating to the brightness/darkness, respiration, and pulse which influence the pupil diameter of the viewer, in advance. Then, the viewer's feeling determination device 1 measures the attention pupil diameter of the viewer who views the content when determining the viewer's feeling, and subtracting the reference data from the attention pupil diameter to calculate the pupil diameter (the pupil diameter corresponding to attention) corresponding only to the attention of the viewer is calculated.

The reception unit 20 receives the visual image a, the eyeball movement image b, the brightness data c, the respiration data d, and the pulse data e from the gaze and pupil diameter measuring instrument 2 and the transmission device 7 illustrated in FIG. 1 using a predetermined communication method, and outputs these pieces of data to the analysis unit 21.

The analysis unit 21 receives the input of the visual image a, the eyeball movement image b, the brightness data c, the respiration data d, and the pulse data e from the reception unit 20, stores these pieces of data directly in the memory unit 24 when these pieces of data are synchronized or causes these pieces of data to be synchronized with each other based on time data attached to the data when these pieces of data are not synchronized and stores these pieces of synchronized data in the memory unit 24. The analysis unit 21 receives input of the visual image a, the eyeball movement image b, the brightness data c, the respiration data d, and the pulse data e from the reception unit 20 or read these data from the memory unit 24, and performs the following processing based on these synchronized data.

The analysis unit 21 measures a visual-point position St of the viewer with respect to the content (with respect to the screen of the display 8) based on the visual image a and the eyeball movement image b, and measures a pupil diameter Bt of the viewer based on the eyeball movement image b. A method of measuring the visual-point position St and the pupil diameter Bt has been well known, and thus, the description thereof will be omitted here.

The analysis unit 21 handles the brightness data c as a content luminance Ht when the brightness data c indicates brightness of the entire screen, and handles the brightness data c as a visual-point position luminance Tt when the brightness data c indicates brightness of the visual-point position St. Specifically, when the brightness measurement device 3 illustrated in FIG. 1 is positioned by an operator such that brightness of a position corresponding to the predetermined visual-point position St on the screen of the display 8 is measured, the analysis unit 21 inputs the brightness data c at this time and handles the input brightness data c as the visual-point position luminance Tt.

Although it is possible to simultaneously measure the visual-point position St of the viewer at the time of viewing the content, there may be a case where it is difficult to simultaneously measure the visual-point position luminance Tt. In this case, after the visual-point position St is measured, the visual-point position luminance Tt is measured in the state of displaying the content again at a different timing from the viewer's viewing of the content. Specifically, the viewer's feeling determination device 1 measures coordinates of the visual-point position St at the time of viewing the content and stores the coordinates in the memory unit 24. Further, the viewer's feeling determination device 1 reads the coordinates of the visual-point position St from the memory unit 24 in the state where the same content as that at the time of viewing the content is being reproduced and causes the brightness measurement device 3 to track the coordinates, whereby the analysis unit 21 measures the visual-point position luminance Tt.

The analysis unit 21 obtains a respiration cycle $Z1t$ based on the respiration data d, and further, generates respiration state data $Z2t$ including timings of a start of inhalation and a start of exhalation. In addition, the analysis unit 21 obtains a pulse cycle $Z3t$ based on the pulse data e, and further, generates pulse state data $Z4t$ including a timing of a start of pulse.

Here, "t" in the visual-point position St, the pupil diameter Bt, the content luminance Ht, the visual-point position luminance Tt, the respiration cycle $Z1t$, the respiration state data $Z2t$, the pulse cycle $Z3t$, and the pulse state data $Z4t$ represents an elapsed time corresponding to a frame number of the content.

The analysis unit 21 stores the visual-point position St, the pupil diameter Bt, the content luminance Ht, the visual-point position luminance Tt, the respiration cycle $Z1t$, the respiration state data $Z2t$, the pulse cycle $Z3t$, and the pulse state data $Z4t$, which are synchronized with each other, in the memory unit 24, and reads these data from the memory unit 24 as necessary.

At the time of reference data measurement, the analysis unit 21 outputs the visual-point position St, the pupil diameter Bt, the respiration cycle $Z1t$, the respiration state data $Z2t$, the pulse cycle $Z3t$, and the pulse state data $Z4t$ to the reference data measurement unit 22. On the other hand, at the time of feeling determination, the analysis unit 21 outputs the pupil diameter Bt, the content luminance Ht, the visual-point position luminance Tt, the respiration cycle $Z1t$, the respiration state data $Z2t$, the pulse cycle $Z3t$, and the pulse state data $Z4t$ to the measurement unit 23. The time of reference data measurement and the time of feeling determination are set by the viewer or the like.

The reference data measurement unit 22 functions at the time of reference data measurement and measures reference data relating to the pupil of the viewer. The reception unit 20 receives the visual image a and the like in a state where a predetermined reference brightness/darkness screen is displayed on the display 8 (a screen where brightness of the entire screen and brightness of a visual point (center circle) are set to a predetermined luminance), and the analysis unit 21 measures the visual-point position St, the pupil diameter Bt, the respiration cycle $Z1t$, the respiration state data $Z2t$, the pulse cycle $Z3t$, and the pulse state data $Z4t$.

The reference data measurement unit 22 inputs these data from the analysis unit 21 for the reference brightness/darkness screen whose brightness is changed in stages. Then, the reference data measurement unit 22 calculates a reference pupil diameter Csk, a respiration pupil diameter Dskt, and a pulse pupil diameter Eskt, and stores these data in the memory unit 25, thereby generating a reference brightness/darkness response table 60, a reference respiration response table 61, and a reference pulse response table 62. As a result, the reference brightness/darkness response table 60, the reference respiration response table 61, and the reference pulse response table 62 including the reference data on relating to the viewer's pupil are stored in the memory unit 25.

Here, "t" in the respiration pupil diameter Dskt represents an elapsed time synchronized with the respiration state data $Z2t$ in the respiration cycle $Z1t$, and "t" in the pulse pupil diameter Eskt represents an elapsed time synchronized with the pulse state data $Z4t$ in the pulse cycle $Z3t$. Details of the respiration pupil diameter Dskt and the pulse pupil diameter Eskt will be described later.

The measurement unit 23 functions at the time of feeling determination, and measures the pupil diameter excluding the influence of brightness/darkness, respiration, and pulse of the viewer. The reception unit 20 receives the visual image a and the like in a state where predetermined content is displayed on the display 8, and the analysis unit 21 measures the visual-point position St, the pupil diameter Bt, the content luminance Ht, the respiration cycle $Z1t$, the respiration state data $Z2t$, the pulse cycle $Z3t$, and the pulse state data $Z4t$ and stores these measured data in the memory unit 24. In addition, the analysis unit 21 measures the visual-point position luminance Tt indicating the luminance of the visual-point position St and stores the measured visual-point position luminance Tt in the memory unit 24. Then, the analysis unit 21 reads out these data from the memory unit 24, and outputs the pupil diameter Bt, the content luminance Ht, the visual-point position luminance Tt, the respiration cycle Z1$t$, the respiration state data Z2$t$, the pulse cycle Z3$t$, and the pulse state data Z4$t$, which are temporally synchronized with each other, to the measurement unit 23.

The measurement unit 23 receive the input of these data from the analysis unit 21 and specifies the reference pupil diameter Csk, the respiration pupil diameter Dskt, and the pulse pupil diameter Eskt of the visual-point position St (corresponding to the pupil diameter Bt) corresponding to the elapsed time of the content based on the content luminance Ht and the visual-point position luminance Tt, and the reference brightness/darkness response table 60, the reference respiration response table 61, and the reference pulse response table 62, which are stored in the memory unit 25. Then, the measurement unit 23 calculates an attention pupil diameter A1$t$ excluding the influence of respiration and pulse based on the pupil diameter Bt, the reference pupil diameter Csk, the respiration pupil diameter Dskt, and the pulse pupil diameter Eskt, and calculates a pupil diameter corresponding to attention A2$t$ excluding the influence of brightness/darkness, respiration, and pulse. Further, the measurement unit 23 excludes the influence of brightness/darkness, respiration, and pulse and based on the attention pupil diameter A1$t$, the pupil diameter corresponding to attention A2$t$, and the reference pupil diameter Csk, and calculates the attention degrees P1$t$ and P2$t$ with no difference between individuals. Details of the attention pupil diameter A1$t$, the pupil diameter corresponding to attention A2$t$, and the attention degrees P1$t$ and P2$t$ will be described later.

Here, "t" in the attention pupil diameter A1$t$, the pupil diameter corresponding to attention A2$t$, and the attention degrees P1$t$ and P2$t$ represents an elapsed time corresponding to the frame number of the content.

[Entire Flow]

Figure 12:
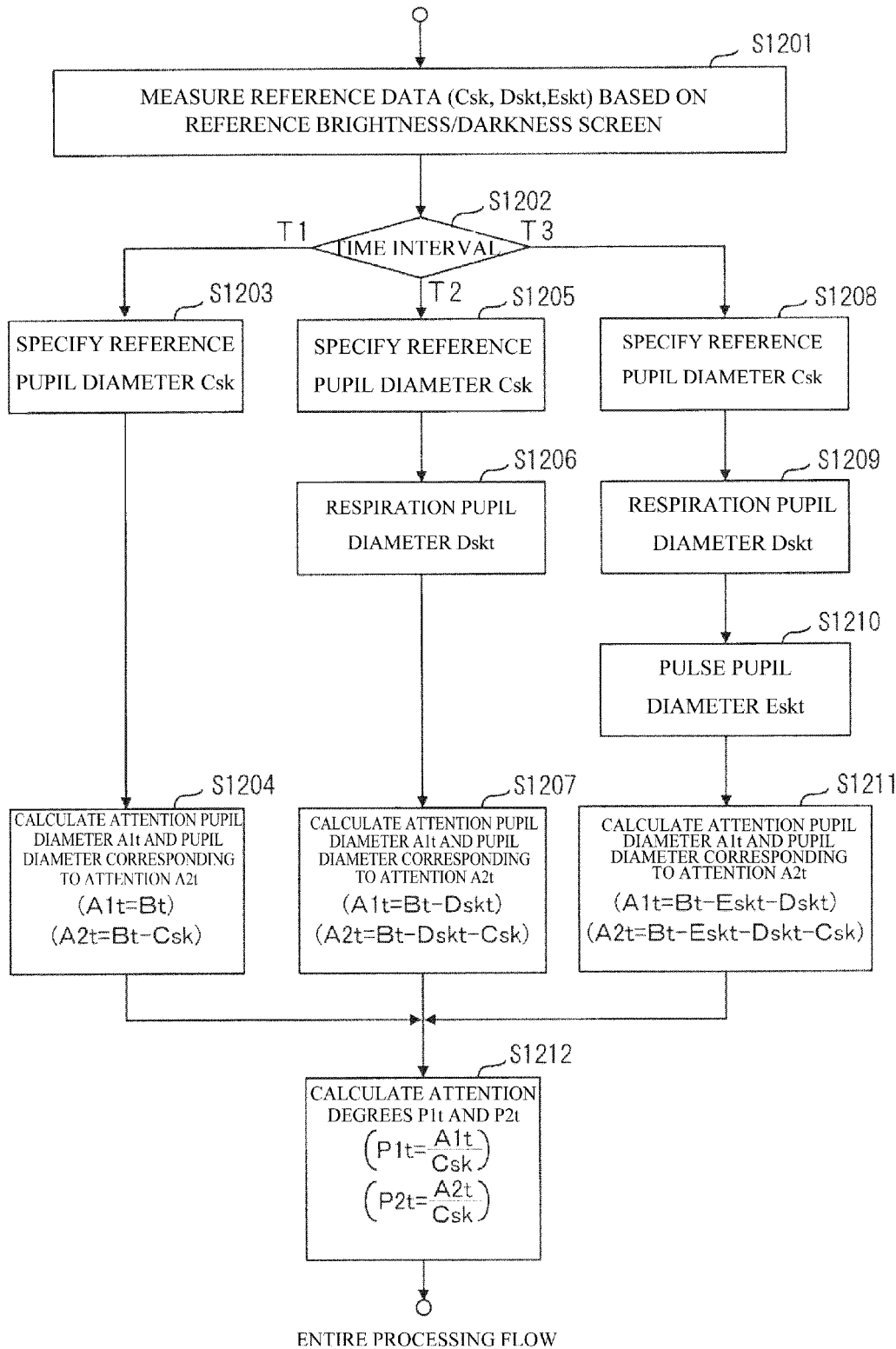
FIG. 12 is a flowchart illustrating the entire processing of the viewer's feeling determination device.

Next, the entire processing of the viewer's feeling determination device 1 illustrated in FIG. 2 will be described. FIG. 12 is a flowchart illustrating the entire processing of the viewer's feeling determination device 1. In FIG. 12, Step S1201 illustrates processing at the time of reference data measurement, and Steps S1202 to S1212 illustrate processing at the time of feeling determination.

First, at the time of reference data measurement, the reference data measurement unit 22 measures the reference data in a state where the reference brightness/darkness screen is displayed on the display 8 with a predetermined brightness of the entire screen and a predetermined brightness of the visual point (the center circle) (Step S1201). As will be described later, a screen in which the brightness of the entire screen and the brightness of the visual point are changed in several stages is used as the reference brightness/darkness screen, and each reference data is measured for the reference brightness/darkness screen of each brightness (each of combinations of the brightness of the entire screen and the brightness of the visual point). The reference data include the reference pupil diameter Csk, the respiration pupil diameter Dskt, and the pulse pupil diameter Eskt, and these pieces of data are stored in the memory unit 25 as the reference brightness/darkness response table 60, the reference respiration response table 61, and the reference pulse response table 62.

At the time of feeling determination, the measurement unit 23 sets time intervals T1, T2, and T3 to determine the feeling in accordance with an instruction set in advance, and shifts to processing according to the time intervals T1, T2, and T3 (Step S1202). The time interval T1 is a predetermined time of two respiration times or more, the time interval T2 is a predetermined time of two pulse times or more and less than two respiration times, and the time interval T3 is a predetermined time less than two pulses. There is a relationship of T1>T2>T3.

In Step S1202, when the time interval is T1 (the time interval of two respiration times or more) (Step S1202: T1), the measurement unit 23 specifies the reference pupil diameter Csk from the reference brightness/darkness response table 60 based on the content luminance Ht indicating the brightness of the content and the visual-point position luminance Tt indicating the brightness of the visual-point position St (Step S1203). Then, the measurement unit 23 sets the pupil diameter Bt (the moving-averaged pupil diameter Bt) for the content to the attention pupil diameter A1$t$ by the following mathematical formula, and subtracting the reference pupil diameter Csk from the pupil diameter Bt to obtain the pupil diameter corresponding to attention A2$t$ (Step S1204).

$$A1t = Bt \quad \text{[Mathematical Formula 1]}$$

$$A2t = Bt - Csk = A1t - Csk \quad \text{[Mathematical Formula 2]}$$

Here, the attention pupil diameter A1$t$ is a value indicating the attention degree of the viewer with respect to the content (a value of the pupil diameter itself at the time of viewing the content), and includes a value of the reference pupil diameter Csk that varies depending on the brightness of the entire screen and the brightness of the visual-point position St. In Mathematical Formula 1, the pupil diameter Bt does not become zero or less and Bt>0 so that the attention pupil diameter A1$t$ also does not become zero or less and A1$t$>0. That is, the attention pupil diameter A1$t$ does not become negative. The same description may also be applied to Mathematical Formulas 3 and 5 to be described later.

On the other hand, the pupil diameter corresponding to attention A2$t$ is a value indicating the degree corresponding only to the attention of the viewer to the content of interest, and from which the value of the reference pupil diameter Csk, which varies depending on the brightness of the entire screen and the brightness of the visual-point position St, is reduced. Therefore, it is also possible to say that the pupil diameter corresponding to attention A2$t$ is a value obtained by excluding the influence of brightness/darkness response.

In the above-described Mathematical Formula 2, when the pupil diameter Bt is smaller than the reference pupil diameter Csk, the pupil diameter corresponding to attention A2$t$ is less than zero and is A2$t$<0, and thus, becomes negative. When the pupil diameter Bt is smaller than the reference pupil diameter Csk, it indicates that the viewer is more bored than when the reference data is measured (reference brightness/darkness response is measured). In addition, when the pupil diameter Bt is larger than the reference pupil diameter Csk, it indicates that the viewer pays more attention than when the reference data is measured (reference brightness/darkness response is measured). The same description may also be applied to Mathematical Formulas 4 and 6 to be described later.

In addition, when the time interval is T2 (a time interval of two pulse times or more and less than two respiration times) (Step S1202: T2) in Step S1202, the measurement unit 23 specifies the reference pupil diameter Csk from the reference brightness/darkness response table 60 and the respiration pupil diameter Dskt from the reference respiration response table 61 based on the content luminance Ht and the visual-point position luminance Tt (Step S1205 and Step S1206). Then, the measurement unit 23 subtracts the respiration pupil diameter Dskt from the moving-averaged pupil diameter Bt by the following mathematical formula to obtain the attention pupil diameter A1$t$, and further, subtracts the reference pupil diameter Csk from a result of the subtraction to obtain the pupil diameter corresponding to attention A2$t$ (Step S1207).

$$A1t=Bt-Dskt \quad \text{[Mathematical Formula 3]}$$

$$A2t=Bt-Dskt-Csk=A1t-Csk \quad \text{[Mathematical Formula 4]}$$

In addition, when the time interval is T3 (a time interval of less than two pulses) (Step S1202: T3) in Step S1202, the measurement unit 23 specifies the reference pupil diameter Csk from the reference brightness/darkness response table 60, the respiration pupil diameter Dskt from the reference respiration response table 61, and the pulse pupil diameter Eskt from the reference pulse response table 62 based on the content luminance Ht and the visual-point position luminance Tt (Step S1208 and Step S1210). Then, the measurement unit 23 subtracts the pulse pupil diameter Eskt from the moving-averaged pupil diameter Bt by the following mathematical formula and subtracting the respiration pupil diameter Dskt from a result of the subtraction to obtain the attention pupil diameter A1$t$, and further, subtracts the reference pupil diameter Csk from a result of the subtraction to obtain the pupil diameter corresponding to attention A2$t$ (Step S1211).

$$A1t=Bt-Eskt-Dskt \quad \text{[Mathematical Formula 5]}$$

$$A2t=Bt-Eskt-Dskt-Csk=A1t-Csk \quad \text{[Mathematical Formula 6]}$$

As a result, the attention pupil diameter A1$t$ excluding the influence of respiration and pulse is calculated, and the pupil diameter corresponding to attention A2$t$ excluding the influence of brightness/darkness, respiration, and pulse is calculated in accordance with the time intervals T1, T2, and T3 in Steps S1204, S1207, and S1211.

The measurement unit 23 shifts from Step S1204, Step S1207 or Step S1211 and divides the attention pupil diameter A1$t$ by the reference pupil diameter Csk according to the following mathematical formula to obtain the attention degree P1$t$, and divides the pupil diameter corresponding to attention A2$t$ by the reference pupil diameter Csk to calculate the attention degree P2$t$ (Step S1212).

$$P1t=A1t/Csk \quad \text{[Mathematical Formula 7]}$$

$$P2t=A2t/Csk=(A1t-Csk)/Csk=A1t/Csk-Csk/Csk=P1t-1 \quad \text{[Mathematical Formula 8]}$$

From the above-described Mathematical Formula 8, the relationship between attention degrees P1$t$ and P2$t$ is obtained according to the following mathematical formula.

$$P1t=P2t+1 \quad \text{[Mathematical Formula 9]}$$

Here, in the above-described Mathematical Formula 7, the attention pupil diameter A1$t$ includes the influence of brightness/darkness response, and the reference pupil diameter Csk also includes the influence of brightness/darkness response under the same condition. Therefore, the attention degree P1$t$ obtained by dividing the attention pupil diameter A1$t$ by the reference pupil diameter Csk is a value from which the brightness/darkness response is eliminated.

The attention degree P1$t$ is a ratio indicating which level of the magnitude of the pupil diameter at the time of attention has with respect to the reference pupil diameter Csk. On the other hand, the attention degree P2$t$ is the proportion of the pupil diameter corresponding only to the attention with respect to the reference pupil diameter Csk. Since the attention pupil diameter A1$t$>0 as described above, the attention degree P1$t$>0. On the other hand, there is a case where the pupil diameter corresponding to attention A2$t$<0 so that there is a case where the attention degree P2$t$<0.

The attention degree P1$t$ can be used when it is difficult to handle a negative number in the calculation of audience quality or the like in the above-described Patent Literature 2. As can be seen from the above-described Mathematical Formula 7, a reference value of the attention degree P1$t$ is "1".

On the other hand, a reference value of the attention degree P2$t$ is "0", and the viewer pays more attention than the usual time of reference data measurement when the attention degree P2$t$ is positive, and is more bored at the usual time of reference data measurement when the attention degree P2$t$ is negative. Therefore, the attention degree P2$t$ can be used in the case of determining whether attention is paid more than the usual time.

Figure 24:
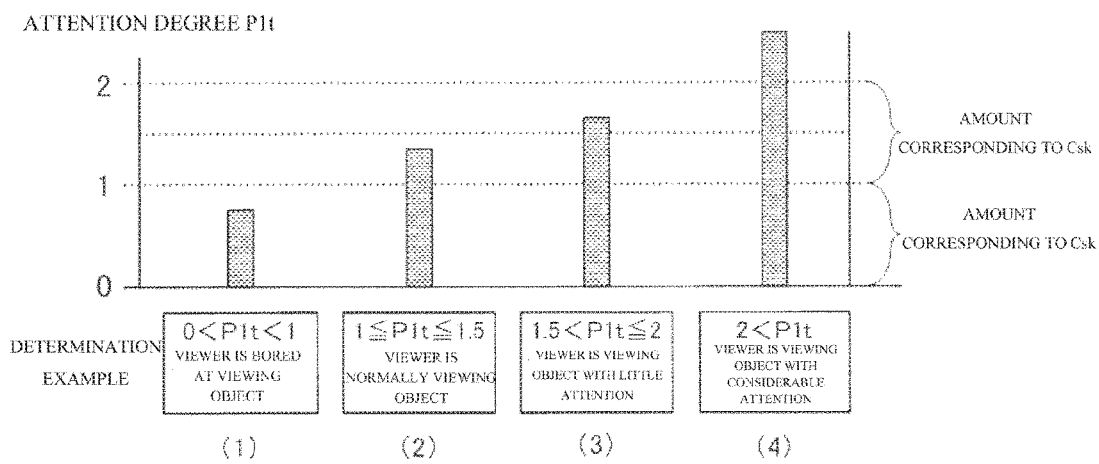
FIG. 24 is a view illustrating a determination example based on an attention degree P1t when a visual object is viewed.

FIG. 24 is a view illustrating a determination example based on the attention degree P1$t$ when the visual object is viewed. As described above, the attention degree P1$t$ is the ratio indicating which level of magnitude the pupil diameter at the time of attention has with respect to the reference pupil diameter Csk. In other words, the pupil diameter Bt at the time of feeling determination indicates the magnification of the pupil diameter enlarged with respect to the reference pupil diameter Csk at the time of reference data measurement under the same luminance condition. Therefore, the attention degree P1$t$=1 represents that the pupil diameter Bt is the same as the reference pupil diameter Csk.

FIG. 24(1) illustrates a case where 0<P1$t$<1, and the measurement unit 23 determines that the viewer is bored at viewing the content. FIG. 24(2) illustrates a case where 1≤P1$t$≤1.5, and the measurement unit 23 determines that the viewer is viewing the content normally. FIG. 24(3) illustrates a case of 1.5<P1$t$≤2, and the measurement unit 23 determines that the viewer is viewing the content with a little attention. FIG. 24(4) illustrates a case of 2<P1$t$, and the measurement unit 23 determines that the viewer is viewing the content with considerable attention.

Figure 25:
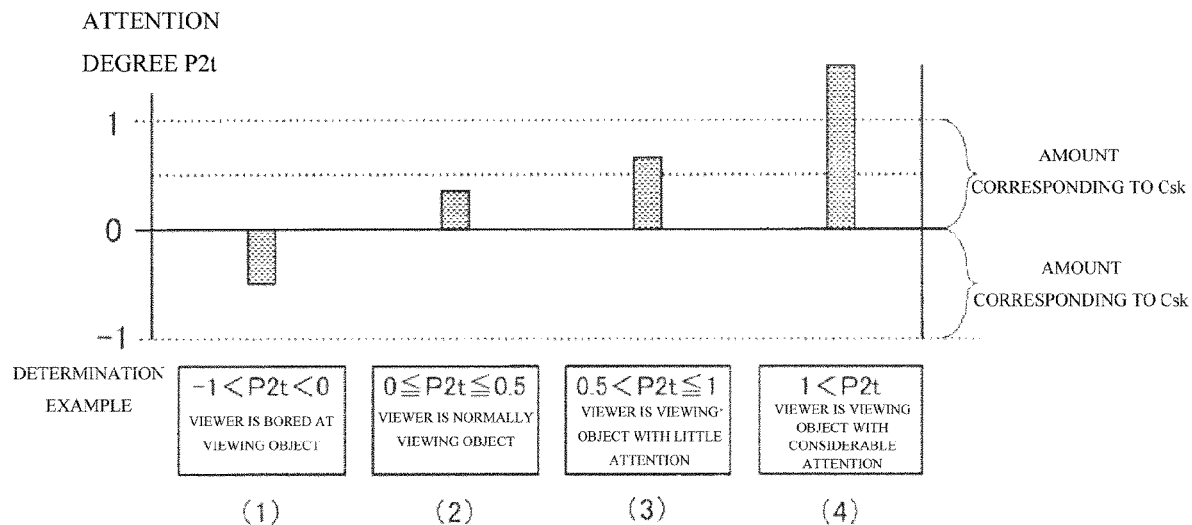
FIG. 25 is a view illustrating a determination example based on an attention degree P2t when the visual object is viewed.

FIG. 25 is a view illustrating a determination example based on the attention degree P2$t$ when the visual object is viewed. As described above, the attention degree P2$t$ is the proportion of the pupil diameter corresponding only to the attention with respect to the reference pupil diameter Csk. In other words, the pupil diameter Bt at the time of feeling determination indicates the magnification of the pupil diameter corresponding only to the attention that is enlarged with respect to the reference pupil diameter Csk at the time of reference data measurement under the same luminance condition. Therefore, the attention degree P2$t$=0 represents that the pupil diameter Bt is the same as the reference pupil diameter Csk.

FIG. 25(1) illustrates a case where −1<P2$t$<0, and the measurement unit 23 determines that the viewer is bored at viewing the content. FIG. 25(2) illustrates a case where 0≤P2$t$≤0.5, and the measurement unit 23 determines that the viewer is viewing the content normally. FIG. 25(3) illustrates a case of 0.5<P2$t$≤1, and the measurement unit 23 determines that the viewer is viewing the content with a little attention. FIG. 25(4) illustrates a case of 1<P2$t$, and the measurement unit 23 determines that the viewer is viewing the content with considerable attention.

In this manner, the attention degrees P1t and P2t excluding influences of brightness/darkness, respiration, and pulse are calculated in accordance with the time intervals T1, T2, and T3 in Step S1212 of FIG. 12. The attention degrees P1t and P2t can be handled as objective information comparable among the plurality of viewers, and it is possible to accurately determine the viewer's feeling with respect to the content.

[Reference Data Measurement Unit 22]

Figure 3:
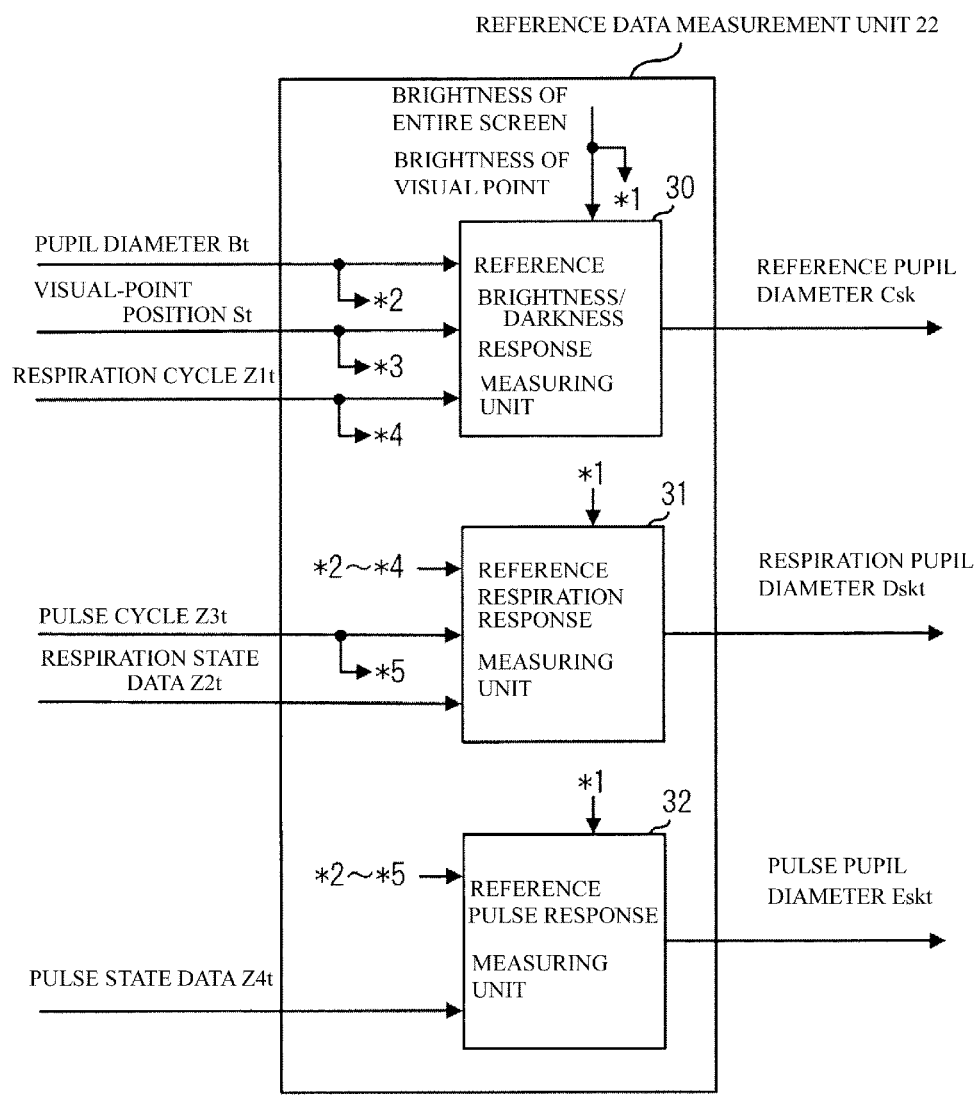
FIG. 3 is a block diagram illustrating a configuration example of a reference data measurement unit.

Next, the reference data measurement unit 22 illustrated in FIG. 2 will be described in detail. FIG. 3 is a block diagram illustrating a configuration example of the reference data measurement unit 22. The reference data measurement unit 22 includes a reference brightness/darkness response measuring unit 30, a reference respiration response measuring unit 31, and a reference pulse response measuring unit 32.

(Reference Brightness/Darkness Screen)

Figures 8, 9:
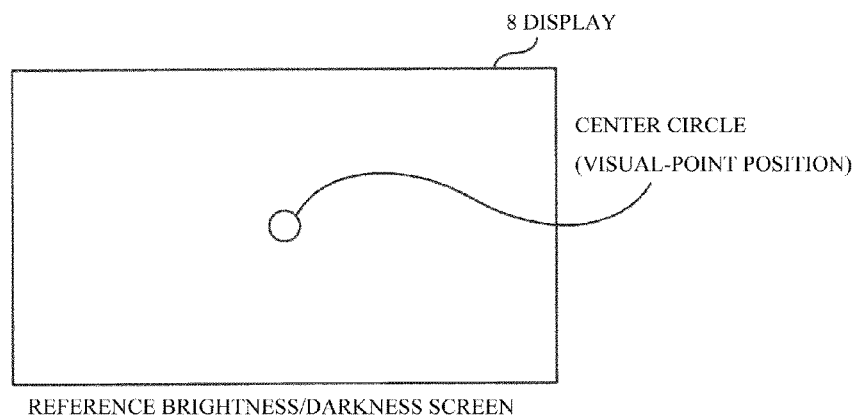
FIG. 8 is a view for describing a reference brightness/darkness screen.
FIG. 9 is a view illustrating a configuration example of a reference brightness/darkness response table.

FIG. 8 is a view for describing the reference brightness/darkness screen. The reference brightness/darkness screen is used when the reference data measurement unit 22 measures the reference data. In general, when a person is viewing the display 8 such as a television, a pupil diameter of a human eye changes with interaction between brightness of the entire screen of the display 8 and brightness of a visual point viewed by the viewer. Therefore, the reference brightness/darkness screen is displayed on the display 8 in order to measure, in advance, the reference data indicating the brightness-darkness response, the respiration response, and the pulse response of the pupil diameter peculiar to the viewer.

As illustrated in FIG. 8, the reference brightness/darkness screen is a screen in which the entire screen of the display 8 is displayed with predetermined brightness (luminance) and the inside of a center circle (1 cm to 2 cm in diameter) in the vicinity of the center of the display 8 with predetermined brightness. At the time of reference data measurement, the reference brightness/darkness screen is displayed on the display 8 to cause the viewer to view the inside of the center circle and place the visual point there. The brightness of the entire screen of the display 8 is changed in stages and the brightness inside the center circle is also changed in stages for each brightness of the entire screen at each stage.

Figure 10:
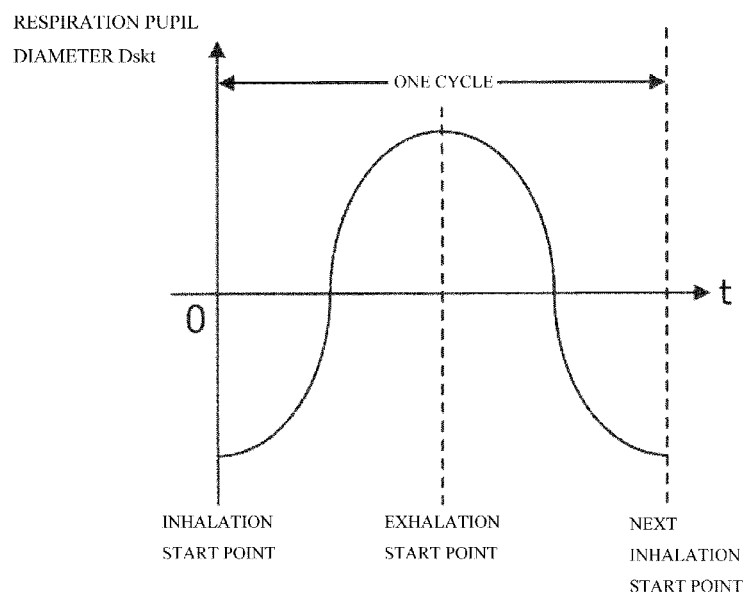
FIG. 10 is a view illustrating a configuration example of a reference respiration response table.
Figure 11:
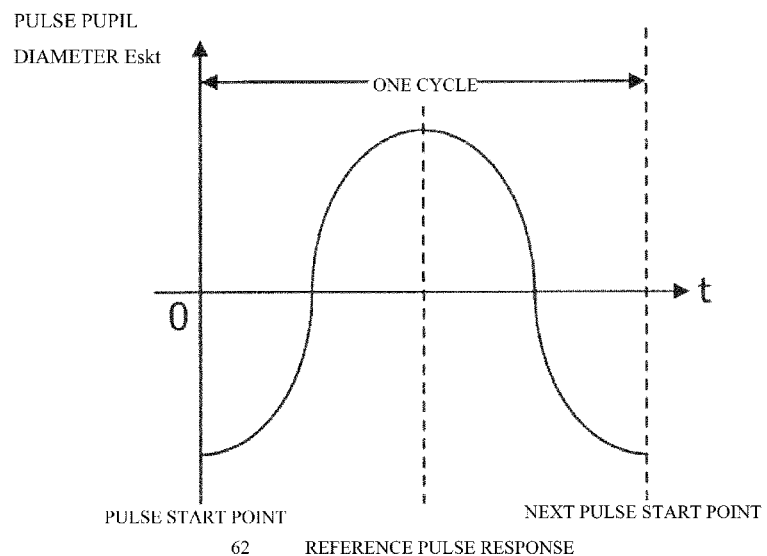
FIG. 11 is a view illustrating a configuration example of a reference pulse response table.

The stepwise change of the brightness of the entire screen is achieved by changing the darkest brightness and the brightest brightness in five stages, for example, of 0%, 25%, 50%, 75%, and 100% as illustrated in FIGS. 9 to 11 to be described later. In addition, the stepwise change of the brightness inside the center circle is achieved by changing the darkest brightness and the brightest brightness in five stages, for example, of 0%, 25%, 50%, 75%, and 100% as illustrated in FIGS. 9 to 11 to be described later in each stage of the brightness of the entire screen. In this case, the stepwise change of the brightness inside the center circle is changed every predetermined time of, for example, 15 seconds or more, which is two respiration times or more, when the respiration cycle of the viewer is set as one respiration time.

Figure 13:
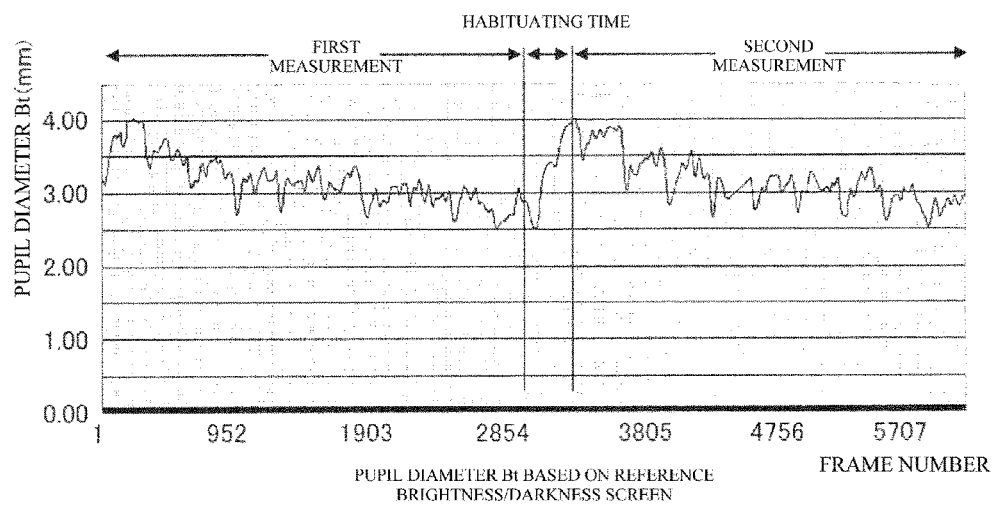
FIG. 13 is a view illustrating an example of a pupil diameter Bt measured by the reference brightness/darkness screen.

Immediately after the brightness of the entire screen has changed to the next stage, for example, a habituating time of three seconds is provided until the change of the pupil diameter of the viewer is settled, and the change of the brightness inside the center circle is fixed at the initial 0% state. The stepwise brightness is repeatedly changed twice as illustrated in FIG. 13 to be described later. The reason why the change is repeated twice under the same condition is that the viewer may pay attention to the screen in the first measurement, and such excessive attention is reflected in the pupil diameter Bt so that it is possible to obtain the highly accurate pupil diameter Bt without such excessive attention in the second measurement. Therefore, the pupil diameter Bt obtained in the second measurement is used to generate the reference brightness/darkness response table 60, the reference respiration response table 61, and the reference pulse response table 62 in which the reference pupil diameter Csk, the respiration pupil diameter Dskt, and the pulse pupil diameter Eskt are reflected. In this case, the stages of brightness may be reduced or time to change the brightness in stages may be shortened in the first measurement as compared to the second measurement.

(Reference Brightness/Darkness Response Measuring Unit 30)

With reference to FIG. 3, the reference brightness/darkness response measuring unit 30 calculates reference pupil diameter Csk which is a brightness-darkness response value of the pupil diameter peculiar to the viewer, and generates the reference brightness/darkness response table 60. Specifically, the reference brightness/darkness response measuring unit 30 receives input of data (0%, 25%, 50%, 75%, and 100%) of the brightness of the entire screen and the brightness of the visual point of the reference brightness/darkness screen used for the current measurement (at the current point in time) among the brightness changing in stages set in advance. Incidentally, the reference brightness/darkness response measuring unit 30 may receive the input of the content luminance Ht as the brightness of the entire screen used for the current measurement, and inputs the visual-point position luminance Tt as the brightness of the visual point used for the current measurement from the analysis unit 21 to convert these input values into in stepwise data (0%, 25%, 50%, 75%, and 100%).

The reference brightness/darkness response measuring unit 30 inputs the pupil diameter Bt, the visual-point position St, and the respiration cycle Z1t, acquired in a state where the reference brightness/darkness screen used for the current measurement has been displayed, and determines that the visual-point position St is present inside the center circle of the reference brightness/darkness screen. Then, the reference brightness/darkness response measuring unit 30 sets the time interval T1 (for example, 15 seconds) of two respiration times or more with the respiration cycle Z1t as one respiration time.

FIG. 13 is a view illustrating an example of the pupil diameter Bt measured by the reference brightness/darkness screen. The horizontal axis represents the elapsed time, which is the frame number of the reference brightness/darkness screen, and the vertical axis represents the pupil diameter Bt. The above-described habituating time is provided between the first measurement and the second measurement. As illustrated in FIG. 13, the pupil diameter Bt is finely wavy, and this pupil diameter Bt includes the change influenced by respiration and pulse.

The reference brightness/darkness response measuring unit 30 performs moving average of the pupil diameter Bt over the time interval T1 of two respiration times or more to obtain the pupil diameter of a moving average value thereof. As a result, it is possible to equalize the change of the pupil diameter that is periodically influenced by the pulse and respiration with respect to the pupil diameter Bt, and it is possible to exclude the influence of pulse and respiration. The moving-averaged pupil diameter is the pupil diameter influenced only by the brightness/darkness.

It is preferable that the time interval T1 of two respiration times or more be nZ1t [sec] (n is an integer of two or more)

when the respiration cycle of the viewer is set as one respiration time ($Z1t$ [sec]). It is unnecessary for T1 to be exactly an integral multiple of $Z1t$. For example, T1 may be ($nZ1t-0.1Z1t$) or more and ($nZ1t+0.1Z1t$) or less (or ($nZ1t-0.05Z1t$) or more and ($nZ1t+0.05Z1t$)) or less). Here, n is an integer of two or more, and may be two or more and ten or less, two or more and five or less, three or more and five or less, and two or more and four or less.

Figure 14:
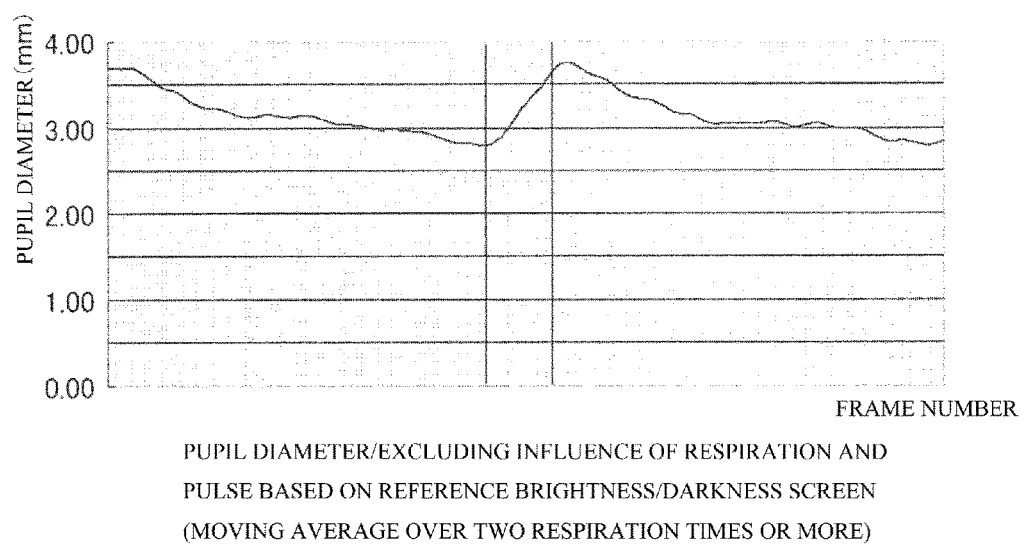
FIG. 14 is a view illustrating an example of a pupil diameter moving-averaged based on two respiration times (a pupil diameter which is influenced by brightness/darkness and from which influence of respiration and pulse is excluded) in FIG. 13.

FIG. 14 is a view illustrating an example of a pupil diameter moving-averaged over the time interval T1 of two respiration times (a pupil diameter which is influenced by brightness/darkness and from which influence of respiration and pulse is excluded) in FIG. 13. As illustrated in FIG. 14, it is understood that the moving-averaged pupil diameter is smooth differently from FIG. 13, and the influence of pulse and respiration is excluded.

The reference brightness/darkness response measuring unit 30 averages the moving-averaged pupil diameter based on time for which the reference brightness/darkness screen with the brightness of the entire screen and the brightness of the visual point used for the current measurement has been displayed to obtain such an average value as the reference pupil diameter Csk. Then, the reference brightness/darkness response measuring unit 30 stores the reference pupil diameter Csk in the memory unit 25, and generates the reference brightness/darkness response table 60.

Here, in the reference pupil diameter Csk, "s" indicates a number of brightness of the visual point changing in stages, and "k" indicates a number of brightness of the entire screen changing in stages. The reference pupil diameter Csk of the reference brightness/darkness response is obtained for each of combinations of the brightness of the entire screen and the brightness of the visual point, which change in stages, by the reference brightness/darkness response measuring unit 30.

FIG. 9 is a view illustrating a configuration example of the reference brightness/darkness response table 60. The reference pupil diameter Csk is stored in the reference brightness/darkness response table 60 for each of combinations of the brightness of the entire screen and the brightness of the visual point which change in stages. The brightness of the visual point which changes in stages is 0% (s=1), 25% (s=2), 50% (s=3), 75% (s=4), and 100% (s=5), and the brightness of the entire screen which changes in stages is 0% (k=1), 25% (k=2), 50% (k=3), 75% (k=4), and 100% (k=5).

As a result, the reference pupil diameter Csk which is the brightness/darkness response value of the pupil diameter peculiar to the viewer is calculated for each of the brightness (k) of the entire screen and the brightness (s) of the visual point, and the reference brightness/darkness response table 60 is generated. Incidentally, the respective five stages are set in the combination of the brightness of the entire screen and the brightness of the visual point in FIG. 9, but the present invention is not limited to the five stages and can be applied to arbitrary stages. The same description may also be applied to FIGS. 10 and 11 to be described later.

(Reference Respiration Response Measuring Unit 31)

Returning to FIG. 3, the reference respiration response measuring unit 31 calculates the respiration pupil diameter Dskt which is a respiration response value of the pupil diameter peculiar to the viewer, and generates the reference respiration response table 61. Specifically, the reference respiration response measuring unit 31 receives input of data (0%, 25%, 50%, 75%, and 100%) of the brightness of the entire screen and the brightness of the visual point of the reference brightness/darkness screen used for the current measurement among the brightness changing in stages set in advance, which is similar to the reference brightness/darkness response measuring unit 30. Incidentally, the reference respiration response measuring unit 31 may receive the input of the content luminance Ht and the visual-point position luminance Tt from the analysis unit 21 to convert these input values into in stepwise data (0%, 25%, 50%, 75%, and 100%), which is similar to the reference brightness/darkness response measuring unit 30.

The reference respiration response measuring unit 31 inputs the pupil diameter Bt, the visual-point position St, the respiration cycle $Z1t$, the respiration state data $Z2t$, and the pulse cycle $Z3t$, acquired in a state where the reference brightness/darkness screen used for the current measurement is displayed, and determines that the visual-point position St is present inside the center circle of the reference brightness/darkness screen. Then, the reference respiration response measuring unit 31 sets the time interval T2 of two pulse times or more and less than two respiration times, with the respiration cycle $Z1t$ as one respiration time and the pulse cycle $Z3t$ as one pulse time.

Assuming that the respiration cycle is one respiration time ($Z1t$ [sec]) and the pulse cycle is one pulse time ($Z3t$), it is preferable to set the predetermined time interval T2 of two pulse times or more and less than two respiration times such that the total of α and β is the minimum when T2 is ($mZ1t-\alpha Z3t$) or more and ($mZ1t+\alpha Z3t$) or less, and ($1-\beta$)$Z1t$ or more and ($1+\beta$)$Z1t$ or less or ($2-\beta$)$Z1t$ or more and less than $2Z1t$. In this manner, it is possible to suppress the variation in the pulse and respiration. (It is preferable that m is an integer of two or more, and $0<\beta<1$)

Figure 15:
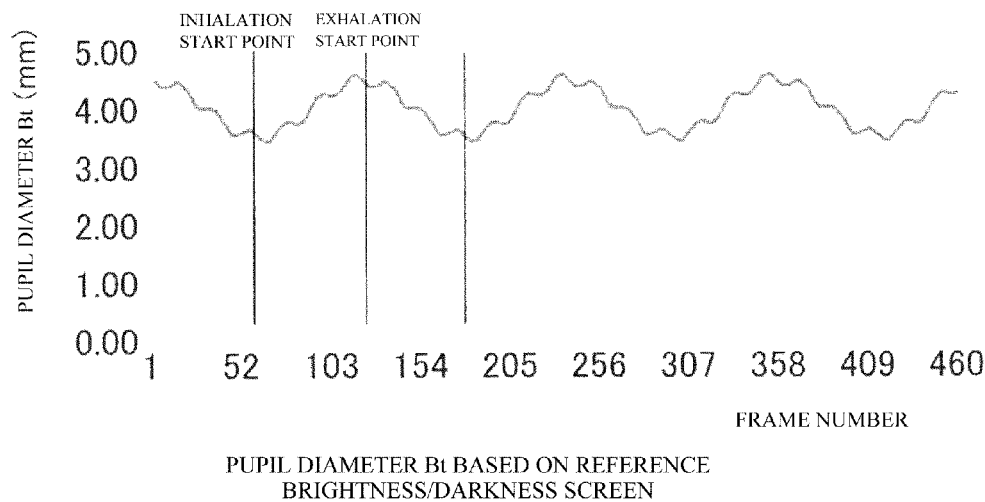
FIG. 15 is a view illustrating an example of the pupil diameter Bt measured by the reference brightness/darkness screen.

FIG. 15 is a view illustrating an example of the pupil diameter Bt measured by the reference brightness/darkness screen, which is the same example as FIG. 13. The horizontal axis represents the elapsed time, which is the frame number of the reference brightness/darkness screen, and the vertical axis represents the pupil diameter Bt. As illustrated in FIG. 15, the waveform of the pupil diameter Bt is periodic and oscillates finely. This pupil diameter Bt includes the change influenced by respiration and pulse. That is, the influence of respiration is reflected in the periodic large fluctuating part, and the influence of pulse is reflected in the fine oscillating part. A time position near the minimum value of the waveform at the pupil diameter Bt represents an inhalation start point and a time position near the maximum value represents an exhalation start point.

The reference respiration response measuring unit 31 performs moving average of the pupil diameter Bt over the time interval T2 of two pulse times or more and less than two respiration times to obtain a pupil diameter as a moving average value thereof. As a result, it is possible to equalize the change of the pupil diameter that is periodically influenced by the pulse with respect to the pupil diameter Bt, and it is possible to exclude the influence of pulse. The moving-averaged pupil diameter is the pupil diameter influenced by brightness/darkness and respiration.

Figure 16:
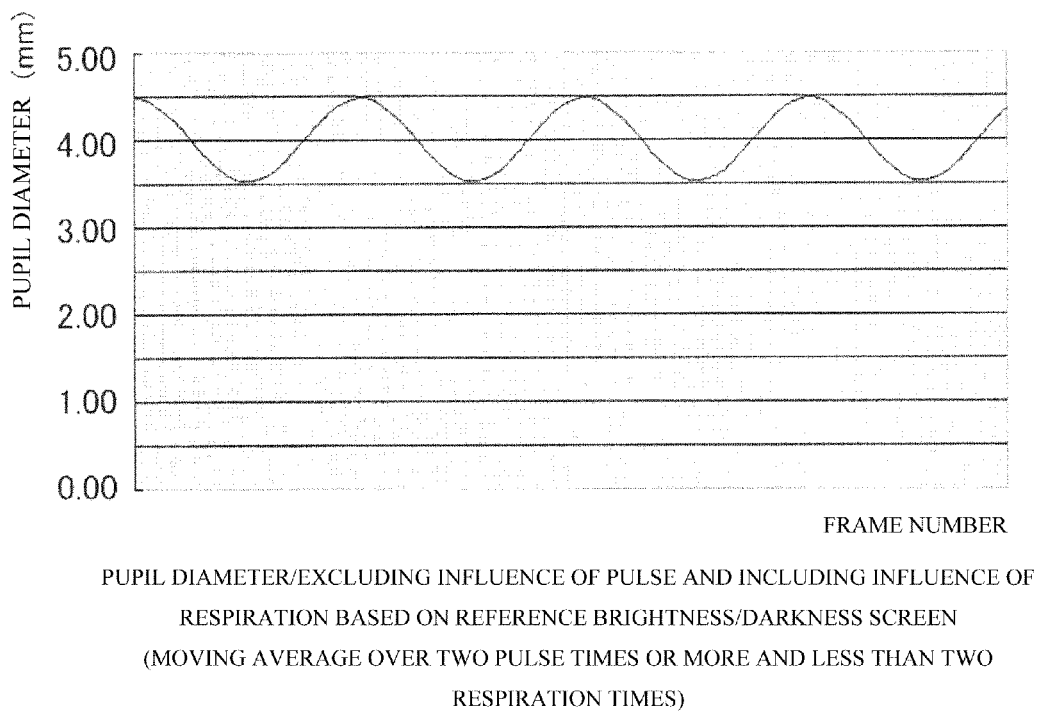
FIG. 16 is a view illustrating an example of a pupil diameter moving-averaged based on two pulse times or more and less than two respiration times (a pupil diameter influenced by respiration and brightness/darkness and from which influences of pulse is excluded) in FIG. 15.

FIG. 16 is a view illustrating an example of a pupil diameter moving-averaged over the time interval T2 of two pulse times or more and less than two respiration times (a pupil diameter influenced by brightness/darkness and respiration and from which influences of pulse is excluded) in FIG. 15. As illustrated in FIG. 16, it is understood that the moving-averaged pupil diameter is smooth differently from FIG. 15, and the influence of pulse is excluded and the influence of respiration remains.

The reference respiration response measuring unit 31 averages the moving-averaged pupil diameter based on time for which the reference brightness/darkness screen with the brightness of the entire screen and the brightness of the visual point used for the current measurement has been displayed to obtain such an average value. In the example of FIG. 16, the average value is about 4 mm. Then, the reference respiration response measuring unit 31 subtracts the average value from the moving-averaged pupil diameter (the pupil diameter moving-averaged over the time interval T2 of two pulse times or more and less than two respiration times) to obtain the pupil diameter influenced only by the respiration which is a result of the subtraction.

Figure 17:
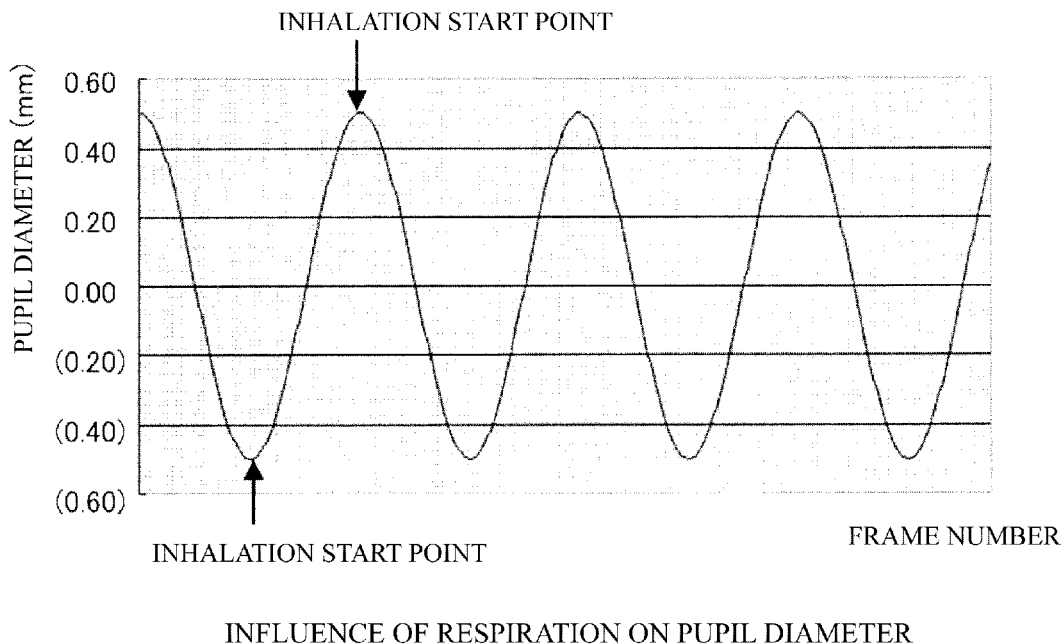
FIG. 17 is a view illustrating a change of the pupil diameter influenced only by the respiration in FIG. 15.

FIG. 17 is a view illustrating the change of the pupil diameter influenced only by the respiration in FIG. 15. This pupil diameter indicates a value that changes depending on the inhalation and exhalation of respiration, and contracts to −0.5 mm at the time of inhalation and expands to +0.5 mm at the time of inhalation when a median value is set to zero.

The reference respiration response measuring unit 31 causes the time of the pupil diameter influenced only by the respiration to be synchronized with the respiration state data $Z2t$ to specify the inhalation start point and the exhalation start point in the time of the pupil diameter influenced only by the respiration. Then, the reference respiration response measuring unit 31 extracts pupil diameters in a time of one cycle of the respiration cycle $Z1t$ including the inhalation start point and the exhalation start point out of the pupil diameters influenced only by the respiration and averages these values to obtain the respiration pupil diameter Dskt. The reference respiration response measuring unit 31 stores the respiration pupil diameter Dskt in the memory unit 25 and generates the reference respiration response table 61.

Here, in the respiration pupil diameter Dskt, "s" and "k" indicate the number of the brightness of the visual point and the number of the brightness of the entire screen which change in stages as described above, and "t" indicates the elapsed time in the time of one cycle of the respiration cycle $Z1t$. The respiration pupil diameter Dskt of the reference respiration response is obtained for each of combinations of the brightness of the entire screen and the brightness of the visual point, which change in stages, by the reference respiration response measuring unit 31.

FIG. 10 is a view illustrating a configuration example of the reference respiration response table 61. The respiration pupil diameter Dskt is stored in the reference respiration response table 61 for each of combinations of the brightness of the entire screen and the brightness of the visual point which change in stages. The brightness of the entire screen and the brightness of the visual point which change in stages are the same as those in FIG. 9. As illustrated in FIG. 10, the respiration pupil diameter Dskt indicates a change of the pupil diameter in the time of one cycle of the respiration cycle $Z1t$, assuming that the inhalation start point is t=0 and the exhalation start point is t=$Z1t$/2. The respiration pupil diameter Dskt (t=0) becomes the minimum when the inspiratory start point is t=0. Incidentally, a temporal change of the respiration pupil diameter Dskt illustrated in FIG. 10 represents not an actual characteristic but an imaginary characteristic.

As a result, the respiration pupil diameter Dskt which is the respiration response value of the pupil diameter peculiar to the viewer is calculated for each of the brightness (k) of the entire screen and the brightness (s) of the visual point, and the reference respiration response table 61 is generated.

(Reference Pulse Response Measuring Unit 32)

Returning to FIG. 3, the reference pulse response measuring unit 32 calculates the pulse pupil diameter Eskt which is a pulse response value of the pupil diameter peculiar to the viewer, and generates the reference pulse response table 62. Specifically, the reference pulse response measuring unit 32 receives input of data (0%, 25%, 50%, 75%, and 100%) of the brightness of the entire screen and the brightness of the visual point of the reference brightness/darkness screen used for the current measurement among the brightness changing in stages set in advance, which is similar to the reference brightness/darkness response measuring unit 30 and the reference respiration response measuring unit 31. Incidentally, the reference pulse response measuring unit 32 may receive the input of the content luminance Ht and the visual-point position luminance Tt from the analysis unit 21 to convert these input values into in stepwise data (0%, 25%, 50%, 75%, and 100%), which is similar to the reference brightness/darkness response measuring unit 30 and the reference respiration response measuring unit 31.

The reference pulse response measuring unit 32 inputs the pupil diameter Bt, the visual-point position St, the respiration cycle $Z1t$, the respiration state data $Z2t$, the pulse cycle $Z3t$, and pulse state data $Z4t$, acquired in a state where the reference brightness/darkness screen used for the current measurement is displayed, and determines that the visual-point position St is present inside the center circle of the reference brightness/darkness screen. Then, the reference pulse response measuring unit 32 sets the time interval T3 of less than two pulses with the respiration cycle $Z1t$ as one respiration time and the pulse cycle $Z3t$ as one pulse time, and sets the time interval T2 of two pulse times or more and less than two respiration times.

The reference pulse response measuring unit 32 performs moving average of the pupil diameter Bt (see FIG. 15) over the time interval T2 of two pulse times or more and less than two respiration times, and calculates the pupil diameter (see FIG. 16) as a moving average value. As a result, it is possible to equalize the change of the pupil diameter that is periodically influenced by the pulse with respect to the pupil diameter Bt, and it is possible to exclude the influence of pulse. The moving-averaged pupil diameter is the pupil diameter influenced by brightness/darkness and respiration.

The reference pulse response measuring unit 32 subtracts the moving-averaged pupil diameter (the pupil diameter moving-averaged over the time interval T2 of two pulse times or more and less than two respiration times) (see FIG. 16) from the pupil diameter Bt (see FIG. 15) in the time for which the reference brightness/darkness screen of the brightness of the entire screen and the brightness of the visual point used for the current measurement has been displayed, thereby obtaining the pupil diameter influenced only by the pulse which is a result of the subtraction.

The reference pulse response measuring unit 32 causes the time of the pupil diameter influenced only by the pulse to be synchronized with the pulse state data $Z4t$ to specify a pulse start point in the time of the pupil diameter influenced only by the pulse. Then, the reference pulse response measuring unit 32 extracts pupil diameters in a time of one cycle of the pulse cycle $Z3t$ including the pulse start point out of the pupil diameters influenced only by the pulse and averages these values to obtain the pulse pupil diameter Eskt. The reference pulse response measuring unit 32 stores the pulse pupil diameter Eskt in the memory unit 25 and generates the reference pulse response table 62.

Here, in the pulse pupil diameter Eskt, "s" and "k" indicate the number of the brightness of the visual point and the number of the brightness of the entire screen which change in stages as described above, and "t" indicates the elapsed time in the time of one cycle of the pulse cycle $Z3t$. The pulse pupil diameter Eskt of the reference pulse response is obtained for each of combinations of the brightness of the entire screen and the brightness of the visual point, which change in stages, by the reference pulse response measuring unit 32.

FIG. 11 is a view illustrating a configuration example of the reference pulse response table 62. The pulse pupil diameter Eskt is stored in the reference pulse response table 62 for each of combinations of the brightness of the entire screen and the brightness of the visual point which change in stages. The brightness of the entire screen and the brightness of the visual point which change in stages are the same as those in FIGS. 9 and 10. As illustrated in FIG. 11, the pulse pupil diameter Eskt indicates a change of the pupil diameter in the time of one cycle of the pulse cycle $Z3t$, assuming that the pulse start point is $t=0$ and the next pulse start point is $t=Z3t$. The pulse pupil diameter Eskt ($t=0$) becomes the minimum when the pulse start point is $t=0$. Incidentally, a temporal change of the pulse pupil diameter Eskt illustrated in FIG. 11 represents not an actual characteristic but an imaginary characteristic.

As a result, the pulse pupil diameter Eskt which is the pulse response value of the pupil diameter peculiar to the viewer is calculated for each of the brightness (k) of the entire screen and the brightness (s) of the visual point, and the reference pulse response table 62 is generated.

[Measurement Unit 23]

Figure 4:
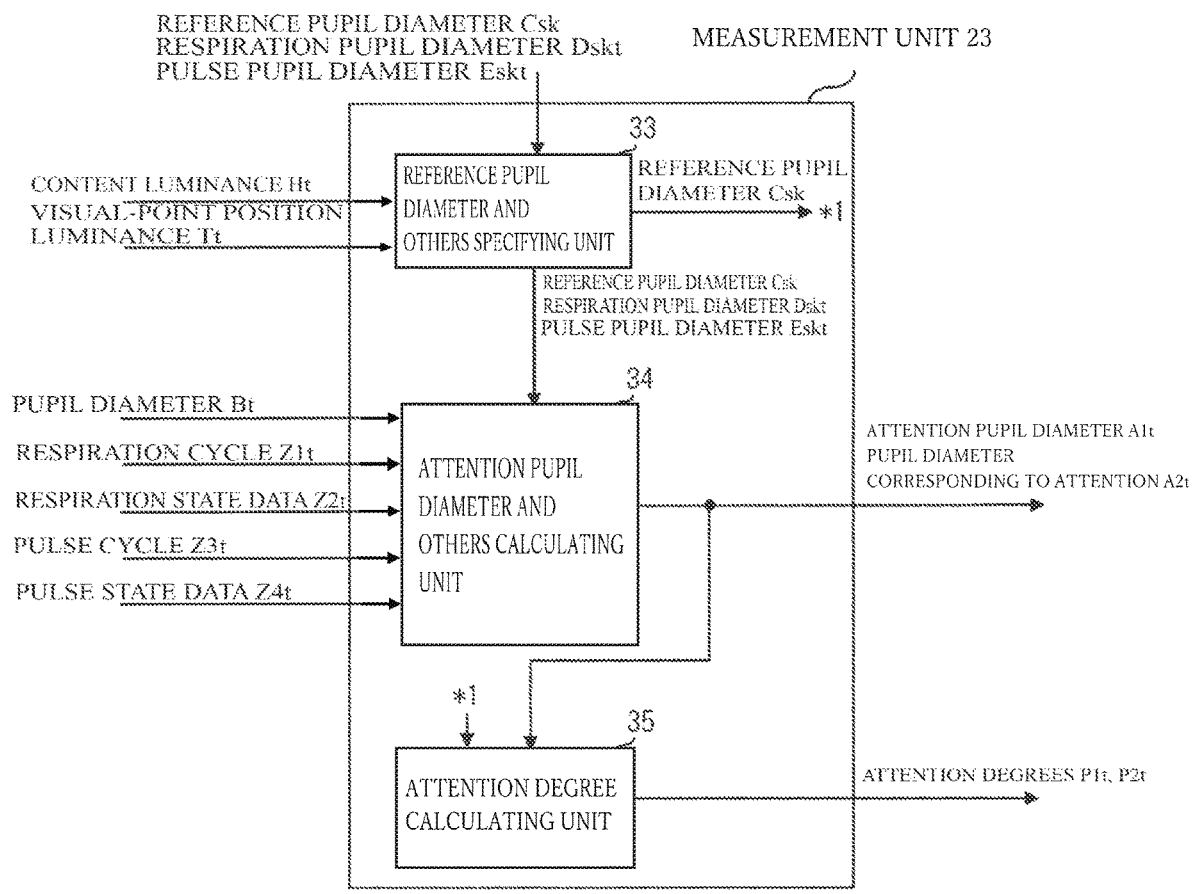
FIG. 4 is a block diagram illustrating a configuration example of a measurement unit.

Next, the measurement unit 23 illustrated in FIG. 2 will be described in detail. FIG. 4 is a block diagram illustrating a configuration example of the measurement unit 23. The measurement unit 23 includes a reference pupil diameter and others specifying unit 33, an attention pupil diameter and others calculating unit 34, and an attention degree calculating unit 35.

The reference pupil diameter and others specifying unit 33 receives input of the content luminance Ht and the visual-point position luminance Tt measured by the analysis unit 21 from the analysis unit 21 with respect to the content displayed on the display 8 at the time of feeling determination. The content luminance Ht is the luminance of the entire screen, and the visual-point position luminance Tt is the luminance of the visual-point position St. After the visual-point position St is measured, the visual-point position luminance Tt is measured in a state where the content are displayed again when it is different from the viewer's viewing of the content. Specifically, the viewer's feeling determination device 1 measures the coordinates of the visual-point position St at the time of viewing the content and stores the coordinates in the memory unit 24 as described above. Further, the viewer's feeling determination device 1 reads the coordinates of the visual-point position St from the memory unit 24 in the state where the same content as that at the time of viewing the content is being reproduced and causes the brightness measurement device 3 to track the coordinates, whereby the analysis unit 21 measures the visual-point position luminance Tt.

Incidentally, when the visual-point position luminance Tt can be measured simultaneously with the viewer's viewing of the content, that is, can be measured simultaneously with the pupil diameter Bt and the like when the content is displayed, the visual-point position luminance Tt is measured in real time. In addition, when there is almost no difference between the luminance of the entire screen and the luminance of the visual-point position and it is difficult to precisely perform the feeling determination, the pupil diameter Bt of the viewer is greatly influenced by the luminance of the entire screen so that the measurement of the luminance of the visual-point position is unnecessary. In this case, the same value as the content luminance Ht is used as the visual-point position luminance Tt. This corresponds to, for example, a case where the content is a general television video or movie. On the other hand, when there is a difference between the luminance of the entire screen and the luminance of the visual-point position, it is necessary to measure the visual-point position luminance Tt for content whose luminance extremely differs between the entire screen and the visual-point position, for example, as a headlight of a car approaches from the dark.

The reference pupil diameter and others specifying unit 33 converts the content luminance Ht and the visual-point position luminance Tt input from the analysis unit 21 into a proportion (%) indicating a stage of the brightness of the entire screen and a proportion (%) indicating a stage of the brightness of the visual point. Then, the reference pupil diameter and others specifying unit 33 retrieves the reference brightness/darkness response table 60, the reference respiration response table 61, and the reference pulse response table 62 stored in the memory unit 25 using the converted proportions indicating the stages of the brightness of the entire screen and the brightness of the visual point as keys.

The reference pupil diameter and others specifying unit 33 selects numbers k and s which are the closest to the converted proportions indicating the stages of the brightness of the entire screen and the brightness of the visual point and specifies the reference pupil diameter Csk, the respiration pupil diameter Dskt, and the pulse pupil diameter Eskt which correspond to the numbers k and s.

As a result, the reference pupil diameter Csk, the respiration pupil diameter Dskt, and the pulse pupil diameter Eskt, which correspond to the content luminance Ht and the visual-point position luminance Tt, are specified. That is, the reference pupil diameter Csk influenced only by the brightness/darkness, the respiration pupil diameter Dskt influenced only by the respiration, and the pulse pupil diameter Eskt influenced only by the pulse are specified with respect to the visual-point position St when the viewer is viewing the reference brightness/darkness screen.

Incidentally, when the brightness of the entire screen and the brightness of the visual point are positioned in the middle of stages of the numbers k and s of the reference brightness/darkness screen, the reference pupil diameter and others specifying unit 33 may select a plurality of corresponding numbers k and s adjacent to each other, and mathematically interpolates the respective reference pupil diameters Csk, respiration pupil diameters Dskt, and pulse pupil diameters Eskt corresponding to the plurality of numbers k and s to specify data in the middle of the stages.

The reference pupil diameter and others specifying unit 33 outputs the specified reference pupil diameter Csk, respiration pupil diameter Dskt, and pulse pupil diameter Eskt to the attention pupil diameter and others calculating unit 34, and outputs the specified reference pupil diameter Csk to the attention degree calculating unit 35.

The attention pupil diameter and others calculating unit 34 receives the input of the reference pupil diameter Csk, the respiration pupil diameter Dskt, and the pulse pupil diameter Eskt, which have been specified corresponding to the visual-point position St when the viewer is viewing the content, from the reference pupil diameter and others specifying unit 33, and receives the input of the pupil diameter Bt, the respiration cycle $Z1t$, the respiration state data $Z2t$, the pulse cycle $Z3t$, and the pulse state data $Z4t$ from the analysis unit 21.

The attention pupil diameter and others calculating unit 34 sets the time intervals T1, T2, and T3 to perform the feeling determination following an instruction set in advance, calculates the attention pupil diameter A1t and the pupil diameter corresponding to attention A2t by processing in accordance with the time intervals T1, T2, and T3, and outputs the attention pupil diameter A1t and the pupil diameter corresponding to attention A2t to the outside and to the attention degree calculating unit 35. Details of the process of calculating the attention pupil diameter A1t and the pupil diameter corresponding to attention A2t in accordance with the time intervals T1, T2, and T3 by the attention pupil diameter and others calculating unit 34 will be described later.

The attention degree calculating unit 35 receives the input of the attention pupil diameter A1t and the pupil diameter corresponding to attention A2t from the attention pupil diameter and others calculating unit 34 and receives the input of the reference pupil diameter Csk from the reference pupil diameter and others specifying unit 33. Then, the attention degree calculating unit 35 obtains the attention degrees P1t and P2t at the time t from the above-described Mathematical Formulas 7 and 8.

As a result, it is possible to obtain the objective attention degrees P1t and P2t without individual differences even though there are individual differences in the attention pupil diameter A1t and the pupil diameter corresponding to attention A2t.

Example 1

Figure 5:
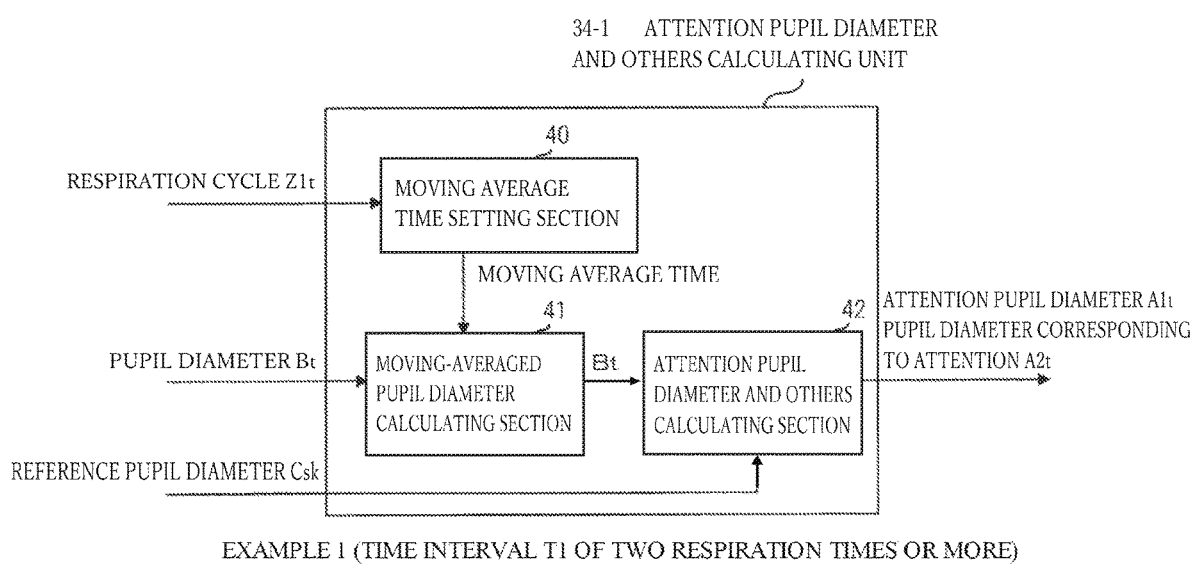
FIG. 5 is a block diagram illustrating a configuration example of an attention pupil diameter and others calculation unit of Example 1.

Next, the attention pupil diameter and others calculating unit 34 of Example 1 illustrated in FIG. 4 will be described in detail. FIG. 5 is a block diagram illustrating a configuration example of the attention pupil diameter and others calculating unit 34 of Example 1. Example 1 is an example of the case where the time interval T1 of two respiration times or more is set as a time interval to determine a feeling, and is configured to determine an emotion that changes relatively gently. An attention pupil diameter and others calculating unit 34-1 includes a moving average time setting section 40, a moving-averaged pupil diameter calculating section 41, and an attention pupil diameter and others calculating section 42.

The moving average time setting section 40 receives input of the respiration cycle Z1t from the analysis unit 21, sets the time interval T1 of two respiration times or more following the instruction set in advance with the respiration cycle Z1t as one respiration time, and handles the time interval T1 as a moving average time. In this case, it is desirable that the moving average time setting section 40 set the same time as the time interval T1 set by the reference data measurement unit 22. The moving average time setting section 40 outputs the moving average time (time interval T1) to the moving-averaged pupil diameter calculating section 41.

The moving-averaged pupil diameter calculating section 41 receives input of the pupil diameter Bt from the analysis unit 21 and receives input of the moving average time (time interval T1) from the moving average time setting section 40, and performs moving average of the pupil diameter Bt based on the moving average time (time interval T1) to obtain a pupil diameter as a moving average value thereof. Here, the same Bt as the pupil diameter Bt input from the analysis unit 21 is used as a reference sign of the moving-averaged pupil diameter for convenience of description.

As a result, it is possible to equalize a change of the pupil diameter that is periodically influenced by pulse and respiration, and it is possible to exclude the influence of pulse and respiration. The moving-averaged pupil diameter Bt is a pupil diameter influenced only by brightness/darkness. Then, the moving-averaged pupil diameter calculating section 41 outputs the pupil diameter Bt as the moving average value to the attention pupil diameter and others calculating section 42.

The attention pupil diameter and others calculating section 42 receives input of the pupil diameter Bt as the moving average value from the moving-averaged pupil diameter calculating section 41 and receives input of the reference pupil diameter Csk from the reference pupil diameter and others specifying unit 33. The attention pupil diameter and others calculating section 42 sets the moving-averaged pupil diameter Bt to the attention pupil diameter A1t (A1t=Bt) as the above-described in Mathematical Formula 1, and subtracts the reference pupil diameter Csk from the pupil diameter Bt as in the above-described Mathematical Formula 2 to obtain the pupil diameter corresponding to attention A2t (A2t=Bt−Csk). The attention pupil diameter and others calculating section 42 outputs the attention pupil diameter A1t and the pupil diameter corresponding to attention A2t to the attention degree calculating unit 35 and to the outside.

In this manner, it is possible to exclude the influence of brightness/darkness by subtracting the reference pupil diameter Csk from the moving-averaged pupil diameter Bt.

The moving-averaged pupil diameter Bt is a pupil diameter which is influenced only by the brightness/darkness and from which the influence of respiration and pulse is excluded for the visual-point position St when the viewer is viewing the content, and the reference pupil diameter Csk is also a pupil diameter which is influenced only by the brightness/darkness and from which the influence of respiration and pulse is excluded for the visual-point position St when the viewer is viewing the reference brightness/darkness screen. Therefore, the pupil diameter corresponding to attention A2t is a pupil diameter from which the influence of brightness/darkness, respiration, and pulse is excluded.

Example 2

Figure 6:
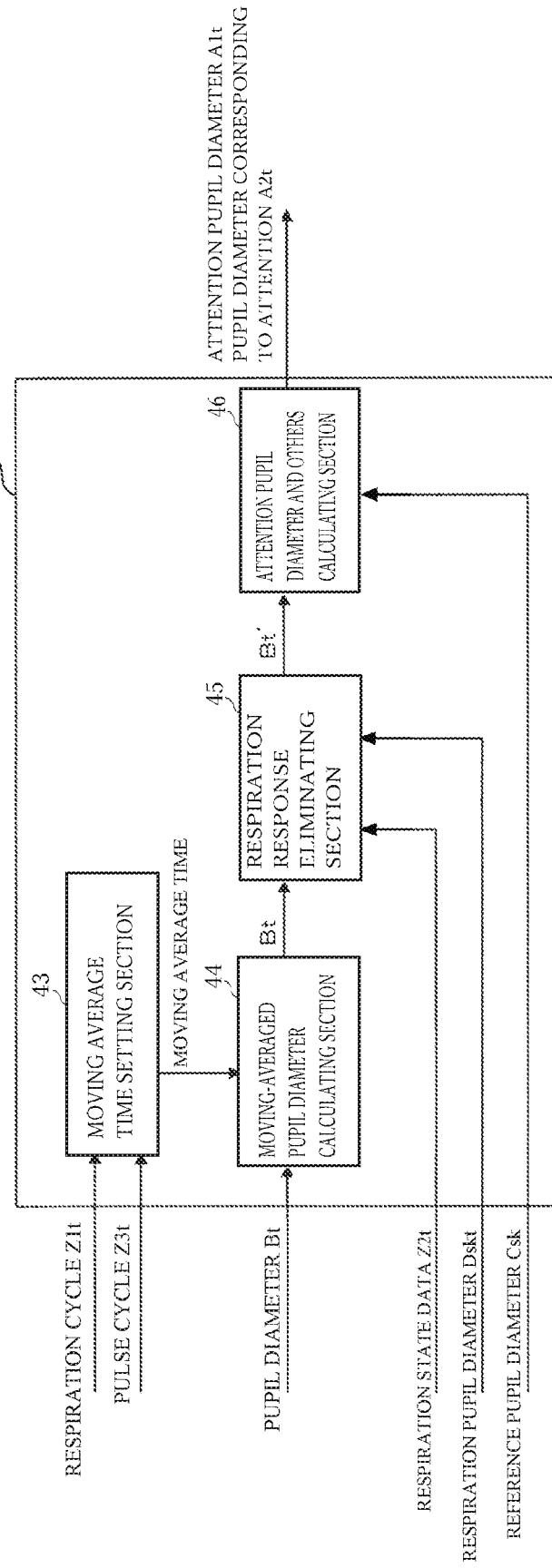
FIG. 6 is a block diagram illustrating a configuration example of an attention pupil diameter and others calculation unit of Example 2.

Next, the attention pupil diameter and others calculating unit 34 of Example 2 illustrated in FIG. 4 will be described in detail. FIG. 6 is a block diagram illustrating a configuration example of the attention pupil diameter and others calculating unit 34 of Example 2. Example 2 is an example of the case where the time interval T2 of two pulse times or more and less than two respiration times is set as a time interval to determine a feeling, and is configured to determine an emotion that changes moderately gently. An attention pupil diameter and others calculating unit 34-2 includes a moving average time setting section 43, a moving-averaged pupil diameter calculating section 44, a respiration response eliminating section 45, and an attention pupil diameter and others calculating section 46.

The moving average time setting section 43 receives input of the respiration cycle Z1t and the pulse cycle Z3t from the analysis unit 21, sets the time interval T2 of two pulse times or more and less than two respiration times with the respiration cycle Z1t as one respiration time and the pulse cycle Z3t as one pulse time following an instruction set in advance, and handles the time interval T2 as a moving average time. In this case, it is desirable that the moving average time setting section 43 set the same time as the time interval T2 set by the reference data measurement unit 22. The moving average time setting section 43 outputs the moving average time (time interval T2) to the moving-averaged pupil diameter calculating section 44.

The moving-averaged pupil diameter calculating section 44 receives input of the pupil diameter Bt from the analysis unit 21 and receives input of the moving average time (time interval T2) from the moving average time setting section 43, and performs moving average of the pupil diameter Bt based on the moving average time (time interval T2) to obtain the pupil diameter Bt as a moving average value thereof. Then, the moving-averaged pupil diameter calculating section 44 outputs the moving-averaged pupil diameter Bt to the respiration response eliminating section 45.

As a result, it is possible to equalize a change of the pupil diameter that is periodically influenced by pulse, and it is possible to exclude the influence of pulse. The moving-averaged pupil diameter Bt is a pupil diameter influenced by brightness/darkness and respiration.

The respiration response eliminating section 45 receives input of the moving-averaged pupil diameter Bt from the moving-averaged pupil diameter calculating section 44, and receives input of the respiration state data Z2$t$ and the respiration pupil diameter Dskt from the analysis unit 21 and the reference pupil diameter and others specifying unit 33, respectively.

The respiration response eliminating section 45 causes the time of the moving-averaged pupil diameter Bt to be synchronized with the respiration state data Z2$t$ to specify an inhalation start point and an exhalation start point in the time of the moving-averaged pupil diameter Bt. The respiration response eliminating section 45 subtracts the respiration pupil diameter Dskt from the moving-averaged pupil diameter Bt by setting the inhalation start point and the exhalation start point in the time of the moving-averaged pupil diameter Bt to correspond to an inhalation start point and an exhalation start point in the time of the respiration pupil diameter Dskt, thereby obtaining a pupil diameter Bt' as a new moving average value. The respiration response eliminating section 45 outputs the pupil diameter Bt' as the new moving average value to the attention pupil diameter and others calculating section 46.

In this manner, it is possible to exclude the influence of respiration by subtracting the respiration pupil diameter Dskt from the moving-averaged pupil diameter Bt.

The moving-averaged pupil diameter Bt is a pupil diameter which is influenced by the brightness/darkness and respiration and from which the influence of pulse is excluded for the visual-point position St when the viewer is viewing the content, and the respiration pupil diameter Dskt is a pupil diameter which is influenced only by the respiration and from which the influence of brightness/darkness and pulse is excluded for the visual-point position St when the viewer is viewing the reference brightness/darkness screen. Therefore, the pupil diameter Bt' as the new moving average value is the pupil diameter from which the influence of respiration and pulse is excluded.

The attention pupil diameter and others calculating section 46 receives input of the pupil diameter Bt' as the moving average value from the respiration response eliminating section 45 and receives input of the reference pupil diameter Csk from the reference pupil diameter and others specifying unit 33. Then, the attention pupil diameter and others calculating section 46 sets the moving-averaged pupil diameter Bt' to the attention pupil diameter A1$t$ (A1$t$=Bt'=Bt−Dskt) as in the above-described Mathematical Formula 3, and further subtracts the reference pupil diameter Csk from the moving-averaged pupil diameter Bt' as in the above-described Mathematical Formula 4 to obtain the pupil diameter corresponding to attention A2$t$ (A2$t$=Bt'−Csk=Bt−Dskt−Csk). The attention pupil diameter and others calculating section 46 outputs the attention pupil diameter A1$t$ and the pupil diameter corresponding to attention A2$t$ to the attention degree calculating unit 35 and to the outside.

In this manner, it is possible to exclude the influence of brightness/darkness by subtracting the reference pupil diameter Csk from the moving-averaged pupil diameter Bt'.

The pupil diameter Bt' as the moving average value is a pupil diameter which is influenced only by the brightness/darkness and from which the influence of respiration and pulse is excluded for the visual-point position St when the viewer is viewing the content, and the reference pupil diameter Csk is also a pupil diameter which is influenced only by the brightness/darkness and from which the influence of respiration and pulse is excluded for the visual-point position St when the viewer is viewing the reference brightness/darkness screen. Therefore, the pupil diameter corresponding to attention A2$t$ is a pupil diameter from which the influence of brightness/darkness, respiration, and pulse is excluded.

Example 3

Figure 7:
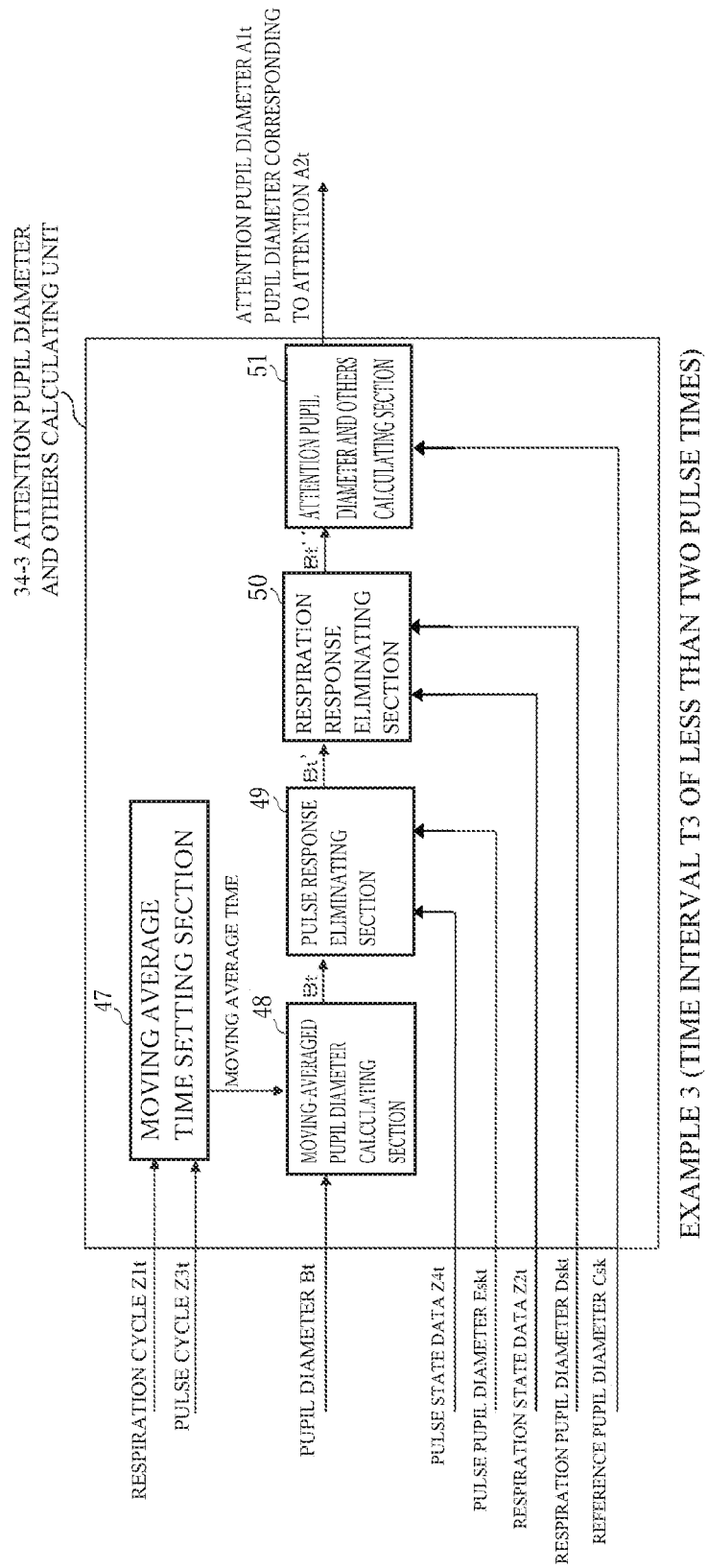
FIG. 7 is a block diagram illustrating a configuration example of an attention pupil diameter and others calculation unit of Example 3.

Next, the attention pupil diameter and others calculating unit 34 of Example 3 illustrated in FIG. 4 will be described in detail. FIG. 7 is a block diagram illustrating a configuration example of the attention pupil diameter and others calculating unit 34 of Example 3. Example 3 is an example of the case where the time interval T3 of less than two pulse times is set as a time interval to determine a feeling, and is configured to determine an emotion that changes in a relatively short time. An attention pupil diameter and others calculating unit 34-3 includes a moving average time setting section 47, a moving-averaged pupil diameter calculating section 48, a pulse response eliminating section 49, a respiration response eliminating section 50, and an attention pupil diameter and others calculating section 51.

The moving average time setting section 47 receives input of the respiration cycle Z1$t$ and the pulse cycle Z3$t$ from the analysis unit 21, sets the time interval T3 of less than two pulse times following an instruction set in advance with the respiration cycle Z1$t$ as one respiration time and the pulse cycle Z3$t$ as one pulse time, and handles the time interval T3 as a moving average time. The moving average time setting section 47 outputs the moving average time (time interval T3) to the moving-averaged pupil diameter calculating section 48.

The moving-averaged pupil diameter calculating section 48 receives input of the pupil diameter Bt from the analysis unit 21 and receives input of the moving average time (time interval T3) from the moving average time setting section 47, and performs moving average of the pupil diameter Bt based on the moving average time (time interval T3) to obtain the pupil diameter Bt as a moving average value thereof. Then, the moving-averaged pupil diameter calculating section 48 outputs the moving-averaged pupil diameter Bt to the pulse response eliminating section 49.

The pulse response eliminating section 49 receives input of the pupil diameter Bt as the moving average value from the moving-averaged pupil diameter calculating section 48, and receives input of the pulse state data Z4$t$ and the pulse pupil diameter Eskt from the analysis unit 21 and the reference pupil diameter and others specifying unit 33 respectively.

The pulse response eliminating section 49 causes the time of the moving-averaged pupil diameter Bt to be synchronized with the pulse state data Z4$t$ to specify the pulse start point in the time of the moving-averaged pupil diameter Bt.

The pulse response eliminating section 49 subtracts the pulse pupil diameter Eskt from the moving-averaged pupil diameter Bt by setting the pulse start point in the time of the moving-averaged pupil diameter Bt to correspond to a pulse start point in the time of the pulse pupil diameter Eskt, thereby obtaining the pupil diameter Bt' as a new moving average value. The pulse response eliminating section 49 outputs the pupil diameter Bt' as the new moving average value to the respiration response eliminating section 50.

In this manner, it is possible to exclude the influence of pulse by subtracting the pulse pupil diameter Eskt from the moving-averaged pupil diameter Bt.

Similarly to the pupil diameter Bt, the pupil diameter Bt as the moving average value is a pupil diameter which is influenced by brightness/darkness, respiration, and pulse for the visual-point position St when the viewer is viewing the content, and the pulse pupil diameter Eskt is a pupil diameter which is influenced only by the pulse and from which the influence of brightness/darkness and respiration is excluded for the visual-point position St when the viewer is viewing the reference brightness/darkness screen. Therefore, the pupil diameter Bt' as the new moving average value is the pupil diameter which is influenced by the brightness/darkness and respiration and from which the influence of pulse is excluded.

The respiration response eliminating section 50 receives input of the pupil diameter Bt' as the moving average value from the pulse response eliminating section 49, and receives input of the respiration state data Z2t and the respiration pupil diameter Dskt from the analysis unit 21 and the reference pupil diameter and others specifying unit 33, respectively.

The respiration response eliminating section 50 performs the same processing as the respiration response eliminating section 45 illustrated in FIG. 6, and subtracts the respiration pupil diameter Dskt from the moving-averaged pupil diameter Bt' to obtain a pupil diameter Bt" as a new moving average value. The respiration response eliminating section 50 outputs the pupil diameter Bt" as the new moving average value to the attention pupil diameter and others calculating section 51.

In this manner, it is possible to exclude the influence of respiration by subtracting the respiration pupil diameter Dskt from the moving-averaged pupil diameter Bt'.

The moving-averaged pupil diameter Bt' is a pupil diameter which is influenced by the brightness/darkness and respiration and from which the influence of pulse is excluded for the visual-point position St when the viewer is viewing the content, and the respiration pupil diameter Dskt is a pupil diameter which is influenced by the respiration and from which the influence of brightness/darkness and pulse is excluded for the visual-point position St when the viewer is viewing the reference brightness/darkness screen. Therefore, the pupil diameter Bt" as the new moving average value is the pupil diameter which is influenced by the brightness/darkness and from which the influence of respiration and pulse is excluded.

The attention pupil diameter and others calculating section 51 receives input of the pupil diameter Bt" as the moving average value from the respiration response eliminating section 50 and receives input of the reference pupil diameter Csk from the reference pupil diameter and others specifying unit 33. Then, the attention pupil diameter and others calculating section 51 sets the pupil diameter Bt" as the moving average value to the attention pupil diameter A1t (A1t=Bt"=Bt−Eskt−Dskt) as in the above-described Mathematical Formula 5, and further subtracts the reference pupil diameter Csk from the moving-averaged pupil diameter Bt" to obtain the pupil diameter corresponding to attention A2t (A2t=Bt"−Csk=Bt−Eskt−Dskt−Csk) as in the above-described Mathematical Formula 6. The attention pupil diameter and others calculating section 51 outputs the attention pupil diameter A1t and the pupil diameter corresponding to attention A2t to the attention degree calculating unit 35 and to the outside.

In this manner, it is possible to exclude the influence of pulse and respiration by setting the moving-averaged pupil diameter Bt" to the attention pupil diameter A1t. In addition, it is possible to exclude the influence of brightness/darkness by subtracting the reference pupil diameter Csk from the moving-averaged pupil diameter Bt".

The moving-averaged pupil diameter Bt" is the pupil diameter which is influenced only by the brightness/darkness and from which the influence of respiration and pulse is excluded for the visual-point position St when the viewer is viewing the content, and serves as the attention pupil diameter A1t. The reference pupil diameter Csk is also the pupil diameter which is influenced only by the brightness/darkness and from which the influence of respiration and pulse is excluded for the visual-point position St when the viewer is viewing the reference brightness/darkness screen under the same condition. Therefore, the pupil diameter corresponding to attention A2t is a pupil diameter from which the influence of brightness/darkness, respiration, and pulse is excluded.

Example 4/Mixed Type

Next, the attention pupil diameter and others calculating unit 34 of Example 4 illustrated in FIG. 4 will be described in detail. Example 4 is an example obtained by mixing the attention pupil diameter and others calculating unit 34-1 of Example 1 illustrated in FIG. 5, the attention pupil diameter and others calculating unit 34-2 of Example 2 illustrated in FIG. 6, and the attention pupil diameter and others calculating unit 34-3 of Example 3 illustrated in FIG. 7, and in which an emotion changing relatively gently is determined, an emotion changing moderately gently is determined, or an emotion changing in a relatively short time is determined with respect to single content.

The attention pupil diameter and others calculating unit 34 includes the attention pupil diameter and others calculating units 34-1 to 34-3. In the case of determining the emotion changing relatively gently, the attention pupil diameter and others calculating unit 34 functions as the attention pupil diameter and others calculating unit 34-1, sets the time interval T1 of two respiration times or more, and calculates the attention pupil diameter A1t and the pupil diameter corresponding to attention A2t without considering the respiration and pulse. In addition, in the case of determining the emotion changing moderately gently, the attention pupil diameter and others calculating unit 34 functions as the attention pupil diameter and others calculating unit 34-2, sets the time interval T2 of two pulse times or more and less than two respiration times, and calculates the attention pupil diameter A1t and the pupil diameter corresponding to attention A2t by considering the respiration without considering the pulse. In addition, in the case of determining the emotion changing in a relatively short time, the attention pupil diameter and others calculating unit 34 functions as the attention pupil diameter and others calculating unit 34-3, and calculates the attention pupil diameter A1t and the pupil diameter corresponding to attention A2t by considering the respiration and pulse.

As described above, the reference brightness/darkness screen is displayed on the display 8, and the brightness of the entire screen and the brightness of the visual point of the reference brightness/darkness screen are changed in several stages with the lapse of time at the time of reference data measurement according to the viewer's feeling determination device 1 of the embodiment of the present invention. The reference data measurement unit 22 measures the reference pupil diameter Csk influenced only by the brightness/darkness, the respiration pupil diameter Dskt influenced only by the respiration, and the pulse pupil diameter Eskt influenced only by the pulse for each brightness. Then, the reference data measurement unit 22 generates the reference brightness/darkness response table 60, the reference respiration response table 61, and the reference pulse response table 62.

At the time of feeling determination, in a state where predetermined content is displayed on the display 8, the measurement unit 23 specifies the reference pupil diameter Csk, the respiration pupil diameter Dskt, and the pulse pupil diameter Eskt corresponding to the elapsed time of the content (corresponding to the pupil diameter Bt) based on the content luminance Ht, the visual-point position luminance Tt, the reference brightness/darkness response table 60, the reference respiration response table 61, and the reference pulse response table 62.

When the time interval is T1 (the time interval of two respiration times or more), the measurement unit 23 sets the moving-averaged pupil diameter Bt to the attention pupil diameter A1$t$, and further, subtracts the reference pupil diameter Csk from the attention pupil diameter A1$t$ to obtain the pupil diameter corresponding to attention A2$t$. In addition, when the time interval is T2 (the time interval of two pulse times or more and less than two respiration times), the measurement unit 23 subtracts the pulse pupil diameter Eskt from the pupil diameter Bt and subtracts the respiration pupil diameter Dskt from a result of the subtraction to obtain the attention pupil diameter A1$t$, and further, subtracts the reference pupil diameter Csk from the attention pupil diameter A1$t$ to obtain the pupil diameter corresponding to attention A2$t$. In addition, when the time interval is T3 (the time interval of less than two pulses), the measurement unit 23 subtracts the pulse pupil diameter Eskt from the moving-averaged pupil diameter Bt and subtracts the respiration pupil diameter Dskt from a result of the subtraction to obtain the attention pupil diameter A1$t$, and further, subtracts the reference pupil diameter Csk from the attention pupil diameter A1$t$ to obtain the pupil diameter corresponding to attention A2$t$. As a result, the pupil diameter corresponding to attention A2$t$ excluding the influence of brightness/darkness, respiration, and pulse is calculated in accordance with the time intervals T1, T2, and T3.

Then, the measurement unit 23 divides the attention pupil diameter A1$t$ and the pupil diameter corresponding to attention A2$t$ by the reference pupil diameter Csk to obtain the attention degrees P1$t$ and P2$t$. As a result, the attention degrees P1$t$ and P2$t$ excluding the influence of brightness/darkness, respiration, and pulse are calculated in accordance with the time intervals T1, T2, and T3.

Therefore, it is possible to measure the pupil diameter excluding the influence of brightness/darkness, respiration, and pulse with respect to the viewer viewing the content displayed on the display 8, and to more accurately determine the viewer's feeling.

[Viewer's Feeling Determination System/Example of Viewing Object in Open Environment]

First, another viewer's feeling determination system including the viewer's feeling determination device according to the embodiment of the present invention will be described. In this example, a feeling of a viewer is determined in a case where the viewer views an object in open environment, and the viewer is assumed to move in the environment where there is no change in the ambient light.

Figure 18:
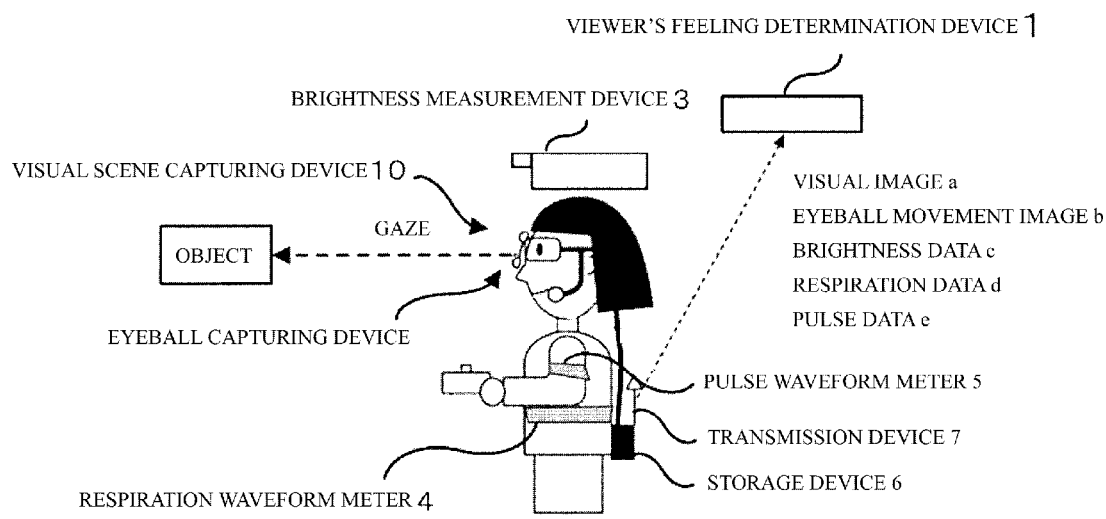
FIG. 18 is a schematic view illustrating a configuration example of another viewer's feeling determination system including a viewer's feeling determination device according to the embodiment of the present invention.

FIG. 18 is a schematic view illustrating a configuration example of another viewer's feeling determination system including the viewer's feeling determination device according to the embodiment of the present invention. This viewer's feeling determination system is configured to include the viewer's feeling determination device 1, the brightness measurement device 3, the respiration waveform meter 4, the pulse waveform meter 5, the storage device 6, the transmission device 7, an eyeball capturing device 9, and a viewing scene capturing device 10. In FIG. 18, the same parts common to those of FIG. 1 will be denoted by the same reference numerals as those in FIG. 1, and a detailed description thereof will be omitted.

The eyeball capturing device 9 captures an eyeball of the viewer and acquires the eyeball movement image b to measure a visual-point position and a pupil diameter. The viewing scene capturing device 10 captures a scene including the object viewed by the viewer and acquires the visual image a. The eyeball movement image b acquired by the eyeball capturing device 9 and the visual image a acquired by the viewing scene capturing device 10 are stored in the storage device 6 and transmitted to the viewer's feeling determination device 1 by the transmission device 7.

When the viewer walks outdoors under the cloudy sky or walks indoors with the same brightness, it is possible to compare the attention degree by comparing pupil diameters. For example, when the viewer walks in the town, it is possible to use the present invention for verification when comparing a noticeable degree of a displayed object such as a prominent signboard or comparing a noticeable degree of the commodity display.

In this case, it is necessary to perform moving average of the pupil diameter Bt over the time interval T1 of two respiration times or more assuming that the viewer moves in the environment where there is no change in the ambient light, in order to exclude the influence of respiration and pulse. On the other hand, when the brightness of the object also changes in environment where the ambient light changes, reference data corresponding to a change in brightness is measured using the configuration and processing of the viewer's feeling determination device 1 illustrated in FIG. 2, and performs moving average of the pupil diameter Bt over the time intervals T2 and T3, which are less than two respiration times, to exclude the influence of respiration and the like. The reference brightness/darkness response measuring unit 30 in this case measures reference data on the viewer's pupil for each combination of brightness of the entire reference image and brightness of a visual point when brightness of the entire predetermined reference image including the object and brightness of the visual point are changed in stages.

As described above, according to the viewer's feeling determination device 1 of the embodiment of the present invention, it is possible to measure the pupil diameter excluding the influence of brightness/darkness, respiration, and pulse for the viewer viewing the object in the open environment, and to more accurately determine the viewer's feeling similarly to the viewer's feeling determination device 1 illustrated in FIG. 1 even when the object is viewed in the open environment.

[Plurality of Viewers]

Incidentally, a case of calculating an average value of the attention degree Pt with respect to an object such as content for a plurality of viewers is assumed. When the plurality of viewers view the same object such as the content at the same time, the analysis unit 21 of the viewer's feeling determination device 1 acquires the pupil diameters Bt of the plurality of viewers. Then, the measurement unit 23 sets the pupil diameters Bt of the plurality of viewers input from the analysis unit 21 as the attention pupil diameters At without performing moving average processing and correction processing of the pupil diameter Bt, and calculates each of the attention degrees P1$t$. Then, the measurement unit 23 calculates an average value by adding the attention degrees P1$t$ for each time for the attention degrees P1$t$ of the plurality of viewers.

As a result, mountains and valleys of the attention degrees P1$t$ are offset as the number of viewers increases, and thus, it is possible to exclude influence of periodic individual viewer's respiration and pulse on the attention degree P1$t$, and the average value of the attention degrees P1$t$ for each time is obtained for each population of the plurality of viewers. Therefore, the influence of respiration and pulse on the attention degree P1$t$ decreases as the number of viewers increases.

Application Example

Next, an application example of the viewer's feeling determination device 1 according to the embodiment of the present invention will be described. Hereinafter, an application example in the case of dividing a screen of the display 8 into an answer screen of a questionnaire will be described.

(Case of Dividing Screen of Display 8)

First, an example in which the viewer's feeling determination device 1 according to the embodiment of the present invention is applied to the case of dividing the screen of the display 8 will be described. FIG. 19 is a view illustrating an example in which the screen of the display 8 is divided. As illustrated in FIG. 19, when the display 8 is divided into K×L areas and predetermined content is displayed on the display 8, the viewer's feeling determination device 1 determines a position Dxy of an instantaneous visual point of the viewer and an attention degree Pxy. Here, xy indicates a position of a division area obtained by dividing the display 8 into the K×L areas.

For example, for content such as TV commercials and dramas, the measurement unit 23 of the viewer's feeling determination device 1 obtains a total of attention degrees Q of a plurality of viewers (for example, N people) by the following mathematical formula at the time of determining the viewer's feeling by verifying an attention point of the viewer.

$$Q = \Sigma_{m-1}^{m=n} Qm \quad \text{[Mathematical Formula 10]}$$

Here, Qm indicates an attention degree of an m-th viewer, and the attention degree P1$t$ is used. The attention degree P2$t$ is not valid because has a negative value, but the attention degree P1$t$ has no negative value.

The measurement unit 23 obtains an attention degree distribution (distribution of attention degrees of the division area Dxy) Wxy of viewers with visual points in the division area Dxy by the following mathematical formula.

$$Wxy = Hxy/Q \times 100(\%) \quad \text{[Mathematical Formula 11]}$$

Here, Hxy indicates the total of attention degrees of the viewers who view the division area Dxy.

As a result, for example, when the content is a TV commercial, it is possible to verify which level of the attention degree is concentrated in the division area where characters of a brand exists, which can be applied to commercial design evaluation.

In addition, the measurement unit 23 divides the magnitude of the entire attention degree Q by the number of viewers N to obtain an attention degree R of the entire screen per person by the following mathematical formula.

$$R = Q/N \quad \text{[Mathematical Formula 12]}$$

As a result, it is possible to verify the magnitude of the attention degree of the entire screen per person, and to understand the attention degree on the commercial.

A case of obtaining an average of attention degrees of a specific division area (divided screen) while a specific scene continues is assumed. The measurement unit 23 calculates a total of the degrees Vxy between time (or frame numbers of content) t1 and t2 by the following mathematical formula.

$$Vxy = \int_{t1}^{t2} Wxy \, dt \quad \text{[Mathematical Formula 13]}$$

The measurement unit 23 calculates an attention degree distribution Sxy of the division area Dxy of the scene per unit time of the entire viewer by the following mathematical formula.

$$Sxy = Vxy/(t2-t1)(\%) \quad \text{[Mathematical Formula 14-1]}$$

In addition, the measurement unit 23 calculates a total time S of the attention degree of the scene in the entire screen by the following mathematical formula.

$$S = \int_{t1}^{t2} R \, dt \quad \text{[Mathematical Formula 14-2]}$$

The measurement unit 23 calculates an attention degree F. of the entire screen in the scene per person and per unit time by the following mathematical formula.

$$F = S/(t2-t1) \quad \text{[Mathematical Formula 15]}$$

(Case of Answer Screen of Questionnaire)

Next, an example in which the viewer's feeling determination device 1 according to the embodiment of the present invention is applied to an answer screen of a questionnaire will be described. In general, the attention degree is concentrated on an answer screen when answering a questionnaire. In addition, when the viewer ambiguously knows the answer, the attention degree is also distributed to other answer fields. Therefore, by the distribution of the attention degree, it is possible to know which level of confidence the viewer has in answering based on the distribution of attention degrees. That is, an answering confidence ratio of the questionnaire (the degree of answering ambiguity as an antonym) can be obtained based on the attention degree. The luminance of a questionnaire screen is substantially constant, and thus, the luminance can be unified from the first measurement of the screen, and the pupil diameter peculiar to the viewer of the reference brightness/darkness screen can also be handled as one value. In this case, the attention degree P2$t$ has a negative value so that the attention degree P1$t$ without any negative value is used.

(Example of Two-Choice Questionnaire)

FIG. 20 is a view illustrating a screen example of a two-choice questionnaire. A questionnaire screen viewing time with the attention degree P1$t$ at a certain time t is set as T. A total of attention times (total attention degree) G is calculated by the following mathematical formula.

$$G = \int_{0}^{T} P1t \, dt \quad \text{[Mathematical Formula 16]}$$

The measurement unit 23 of the viewer's feeling determination device 1 calculates a total attention degree Q1 when coordinates (x, y) of the visual-point position St are present inside a question field (a<x<c and b<y<e) (when the viewer is viewing the area of the question field), an attention degree A1 only when the coordinates (x, y) of the visual-point position St are present inside an answer field A (a<x<d and e<y<f) (when the viewer is viewing the area of the answer field A), and an attention degree B1 only when the coordinates (x, y) of the visual-point position St are present inside an answer field B (d<x<c and e<y<f) (when the viewer is viewing the area of the answer field B). Then, the measurement unit 23 calculates the total attention degree G to this question by the following mathematical formula.

$$G = Q1 + A1 + B1 \qquad \text{[Mathematical Formula 17]}$$

The measurement unit 23 calculates a distribution ratio of the attention degree to the answer field A between the answer fields A and B as an answering confidence ratio (whose complement is the answering ambiguity degree) A' by the following mathematical formula.

$$A' = (A1/(A1+B1)) \times 100 (\%) \qquad \text{[Mathematical Formula 18]}$$

In addition, the measurement unit 23 calculates an answering confidence ratio B' of an area of the answer field B by the following mathematical formula.

$$B' = (B1/(A1+B1)) \times 100 (\%) \qquad \text{[Mathematical Formula 19]}$$

Figures 21, 22:
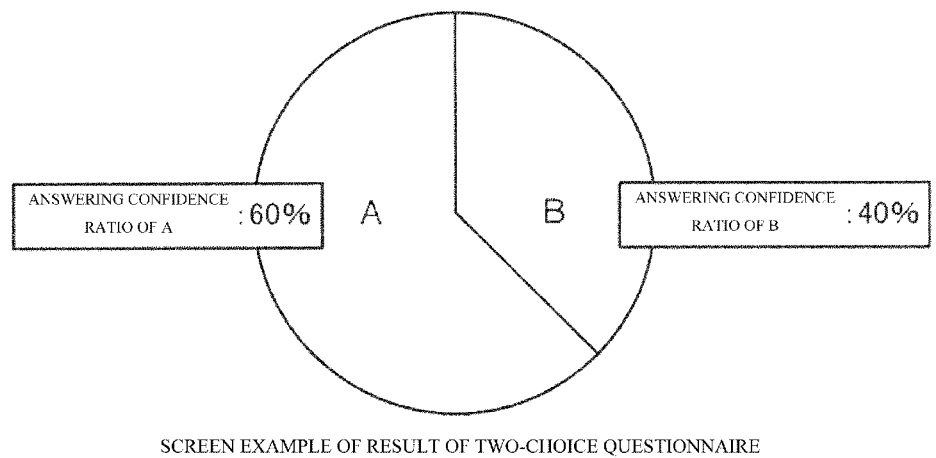
FIG. 21 is a view illustrating a screen example of a result of a two-choice questionnaire.
FIG. 22 is a view illustrating a screen example of a four-choice questionnaire.

FIG. 21 is a view illustrating a screen example of a result of a two-choice questionnaire. As illustrated in FIG. 21, the measurement unit 23 of the viewer's feeling determination device 1 displays the answering confidence ratio of the area A and the answering confidence ratio of the area B with graphs. From the graph of FIG. 21, it is understood that the viewer selects A with 60% of confidence. In addition, it is understood that the viewer is viewing B with 40% of confidence, and the numeric value of 40% means that the viewer has ambiguity at this ratio.

In addition, the measurement unit 23 calculates the total attention degree per unit time of the entire questionnaire screen with the answering time as T by the following mathematical formula.

$$G/T = (Q1+A1+B1)/T \qquad \text{[Mathematical Formula 20]}$$

With this value, it is possible to determine the level of the attention degree (the degree of interest) with respect to this question.

Further, the measurement unit 23 calculates averages (an answering confidence ratio average Aa of the answer field A and an answering confidence ratio average Ba of the answer field B) per person of the questionnaire measurement for a plurality of people N (N is an integer of two or more) by the following mathematical formula $$Aa = (\Sigma_{m=1}^{m=n}(A1/(A1+B1)))/N \times 100(\%) \qquad \text{[Mathematical Formula 21]}$$

$$Ba = (\Sigma_{m=1}^{m=N}(B1/(A1+B1)))/N \times 100(\%) \qquad \text{[Mathematical Formula 22]}$$

The measurement unit 23 calculates an average Qa of the attention degree (degree of interest) of this question per person and per unit time by the following mathematical formula.

$$Qa = (\Sigma_{m=1}^{m=N} G/T)/N \qquad \text{[Mathematical Formula 23]}$$

With this value, it is possible to determine the average attention degree (degree of interest) of the plurality of persons N with respect to this question.

(Example of Four-Choice Questionnaire)

FIG. 22 is a view illustrating a screen example of a four-choice questionnaire. The measurement unit 23 of the viewer's feeling determination device 1 calculates a total attention degree Q1 when coordinates (x, y) of the visual-point position St are present inside a question field (a<x<c and b<y<e) (when the viewer is viewing the area of the question field), an attention degree A1 only when the coordinates (x, y) of the visual-point position St are present inside an answer field A (a<x<d and e<y<f) (when the viewer is viewing the area of the answer field A), an attention degree B1 only when the coordinates (x, y) of the visual-point position St are present inside an answer field B (d<x<c and e<y<f) (when the viewer is viewing the area of the answer field B), an attention degree C1 only when the coordinates (x, y) of the visual-point position St are present inside an answer field C (a<x<d and f<y<g) (when the viewer is viewing the area of the answer field C), and an attention degree D1 only when the coordinates (x, y) of the visual-point position St are present inside an answer field D (d<x<c and f<y<g) (when the viewer is viewing the area of the answer field D). Then, the measurement unit 23 calculates the total attention degree G to this question by the following mathematical formula.

$$G = Q1+A1+B1+C1+D1 \qquad \text{[Mathematical Formula 24]}$$

Further, the measurement unit 23 calculates answering confidence ratios A', B', C', and D' of areas A, B, C, and D by the following mathematical formulas.

$$A' = (A1/(A1+B1+C1+D1)) \times 100(\%)$$

$$B' = (B1/(A1+B1+C1+D1)) \times 100(\%)$$

$$C' = (C1/(A1+B1+C1+D1)) \times 100(\%)$$

$$D' = (D1/(A1+B1+C1+D1)) \times 100(\%) \qquad \text{[Mathematical Formula 25]}$$

Figure 23:
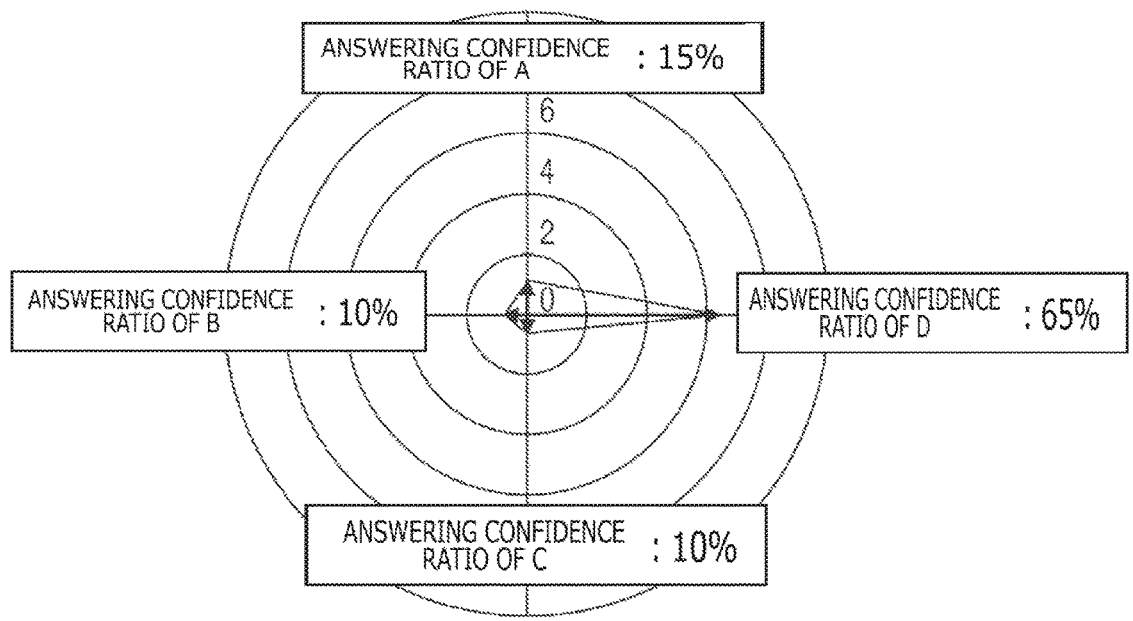
FIG. 23 is a view illustrating a screen example of a result of a four-choice questionnaire.

FIG. 23 is a view illustrating a screen example of a result of the four-choice questionnaire. As illustrated in FIG. 23, the measurement unit 23 of the viewer's feeling determination device 1 displays the answering confidence ratios of the areas A to D with graphs. From the graph of FIG. 23, it is understood that the viewer selects D with 65% of confidence. In addition, it is understood that the viewer is viewing A, B, and C with 15, 10, and 10% of confidence, respectively, and the numeric value of 35% in total means that the viewer has ambiguity at this ratio.

In addition, the measurement unit 23 calculates the total attention degree per unit time of the entire questionnaire screen with the answering time as T by the following mathematical formula.

$$G/T = (Q1+A1+B1+C1+D1)/T \qquad \text{[Mathematical Formula 26]}$$

With this value, it is possible to determine the level of the attention degree (the degree of interest) with respect to this question.

Further, the measurement unit 23 calculates averages (the answering confidence ratio average Aa of the answer field A, the answering confidence ratio average Ba of the answer field B, an answering confidence ratio average Ca of the answer field C, and answering confidence ratio average Da of the answer field D) per person of the questionnaire measurement for a plurality of people N (N is an integer of two or more) by the following mathematical formula.

$$Aa = (\Sigma_{m=1}^{m=N}(A1/(A1+B1+C1+D1)))/N \times 100(\%) \qquad \text{[Mathematical Formula 27]}$$

$$Ba = (\Sigma_{m=1}^{m=N}(B1/(A1+B1+C1+D1)))/N \times 100(\%) \qquad \text{[Mathematical Formula 28]}$$

$$Ca = (\Sigma_{m=1}^{m=N}(C1/(A1+B1+C1+D1)))/N \times 100(\%) \quad \text{[Mathematical Formula 29]}$$

$$Da = (\Sigma_{m=1}^{m=N}(D1/(A1+B1+C1+D1)))/N \times 100(\%) \quad \text{[Mathematical Formula 30]}$$

The measurement unit 23 calculates the average Qa of the attention degree (degree of interest) of this question per person and per unit time by the above-described Mathematical Formula 23. With this value of the average Qa, it is possible to determine the average attention degree (degree of interest) of the plurality of persons N with respect to this question.

Although the present invention has been described by exemplifying the embodiment, the present invention is not limited to the above-described embodiment, and various modifications can be made within a scope not departing from the technical idea thereof. For example, the viewer's feeling determination device 1 illustrated in FIG. 2 may be connected to a network such as the Internet. The viewer's feeling determination device 1 receives an instruction from an external device via the network, and performs the calculation processing of the attention pupil diameter A1t, the pupil diameter corresponding to attention A2t and the attention degrees P1t and P2t, and the like with respect to the predetermined content, the processing in the case of dividing the screen of the display 8, the processing in the case of the questionnaire response screen, and the like based on the instruction. Then, the viewer's feeling determination device 1 transmits processing results to an external device via the network.

In addition, in order to automatically measure the luminance of the visual-point position St of the viewer, the brightness measurement device 3 may cause a measurement direction of the luminance using the brightness measurement device 3 to follow the visual-point position St in the viewer's feeling determination system illustrated in FIGS. 1 and 18.

Specifically, in the viewer's feeling determination system illustrated in FIG. 1, the brightness measurement device 3 includes an actuator that changes an orientation of (a luminance meter provided in) the brightness measurement device 3, and receives input of brightness measurement orientation data g, which will be described later, from the viewer's feeling determination device 1 or the gaze and pupil diameter measuring instrument 2. The brightness measurement orientation data g includes data to cause the orientation of the brightness measurement device 3 to be directed toward the viewer position St of the viewer (for example, data in which the orientation toward the visual-point position St is expressed by polar coordinates with the brightness measurement device 3 as the base point).

The brightness measurement device 3 changes the orientation of the brightness measurement device 3 in the orientation indicated by the brightness measurement orientation data g using the actuator based on the brightness measurement orientation data g. As a result, it is possible to cause the orientation of the brightness measurement device 3 to follow the visual-point position St, and to accurately measure the luminance of the visual-point position St in accordance with the change of the visual-point position St. That is, the viewer's feeling determination device 1 can input the brightness data c which is the luminance of the visual-point position St and automatically and accurately measure the visual-point position luminance Tt in real time (simultaneously with the viewer's viewing of the content).

Incidentally, the brightness measurement device 3 is assumed to be installed near the viewer's head. As the brightness measurement device 3 is installed near the viewer's head, a position of the brightness measurement device 3 and a position of the viewer's eye become close to each other. Thus, the luminance of the visual-point position St is accurately measured by the brightness measurement device 3, and as a result, the visual-point position luminance Tt is accurately measured.

Figure 26:
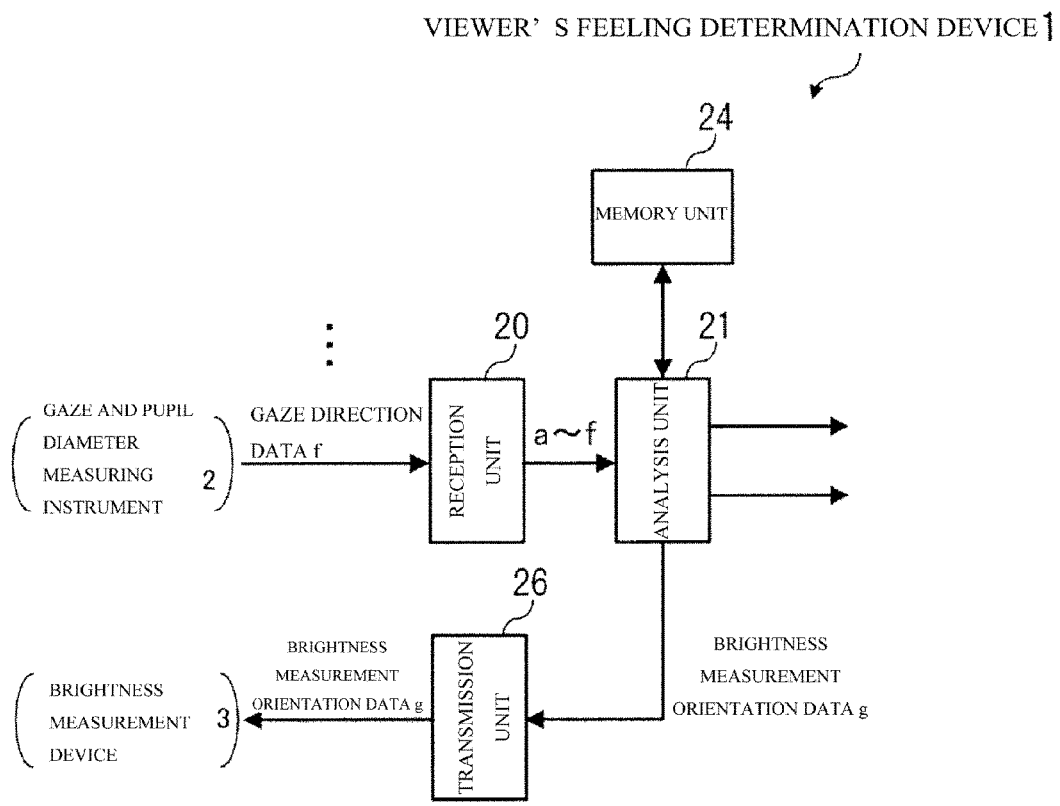
FIG. 26 is a block diagram for describing a first example of automatically measuring a visual-point position luminance Tt.

First, a first example of automatically measuring the visual-point position luminance Tt will be described. FIG. 26 is a block diagram for describing the first example of automatically measuring the visual-point position luminance Tt. In the first example, the viewer's feeling determination device 1 further includes a transmission unit 26 in addition to the components illustrated in FIG. 2.

In addition, with reference to FIG. 1, the gaze and pupil diameter measuring instrument 2 functions as a gaze direction measuring instrument that measures a gaze direction of the viewer. Specifically, the gaze and pupil diameter measuring instrument 2 measures the visual-point position St of the viewer with respect to a visual object (with respect to a screen of the display 8) based on the visual image a and the eyeball movement image b, and measures a direction (gaze direction) of the visual-point position St with the viewer's eye as the base point, thereby generating gaze direction data f. A method of measuring the gaze direction is well known, and for example, a corneal reflection method is used. The gaze direction data f includes data on a direction of a gaze of the viewer (for example, data expressed in polar coordinates with the viewer's eye as the base point). The gaze and pupil diameter measuring instrument 2 transmits the gaze direction data f to the viewer's feeling determination device 1 together with the visual image a and the eyeball movement image b.

With reference to FIG. 26, the reception unit 20 of the viewer's feeling determination device 1 further receives the gaze direction data f in addition to the visual image a and the eyeball movement image b from gaze and pupil diameter measuring instrument 2. Then, the reception unit 20 outputs the gaze direction data f to the analysis unit 21 in addition to the visual image a and the like.

The analysis unit 21 receives the input of the gaze direction data f in addition to the visual image a and the like, and generates the brightness measurement orientation data g based on the gaze direction data f in addition to the above-described processing, and outputs the brightness measurement orientation data g to the transmission unit 26. Specifically, the analysis unit 21 generates the brightness measurement orientation data g by setting the input gaze direction data f directly to the brightness measurement orientation data g.

The transmission unit 26 transmits the brightness measurement orientation data g to the brightness measurement device 3. As a result, the brightness measurement device 3 can receive the brightness measurement orientation data g and cause the orientation of the brightness measurement device 3 to be aligned to the orientation of the visual-point position St based on the brightness measurement orientation data g.

Incidentally, the analysis unit 21 may read correction data corresponding to the gaze direction data f from the memory unit 24 to correct the gaze direction data f based on the correction data and generate the brightness measurement orientation data g. In this case, the gaze direction data f and the correction data corresponding to the gaze direction data f are stored in advance in the memory unit 24.

When the gaze direction data f is used as the brightness measurement orientation data g, the orientation of the brightness measurement device 3 is not necessarily limited to be directed exactly to the visual-point position St. This is because the base point differs therebetween due to a difference between the position of the viewer's eye and the position of the brightness measurement device 3. The correction data is data configured to absorb a difference in spatial position between the position of the viewer's eye as the base point of the gaze direction data f and the position of the brightness measurement device 3 as the base point of the brightness measurement orientation data g and cause the orientation of the brightness measurement device 3 to be accurately directed to the visual-point position St.

As a result, the brightness measurement device 3 can cause the orientation of the brightness measurement device 3 to be accurately aligned to the orientation of the visual-point position St and more accurately measure the luminance of the visual-point position St based on the corrected brightness measurement orientation data g.

In this manner, the viewer's feeling determination device 1 receives the gaze direction data f from the gaze and the pupil diameter measurement device 2, generates the brightness measurement orientation data g based on the gaze direction data f, and transmits the brightness measurement orientation data g to the brightness measurement device 3 according to the first example of automatically measuring the visual-point position luminance Tt. As a result, the brightness measurement device 3 can change the orientation of the brightness measurement device 3 to the orientation of the visual-point position St based on the brightness measurement orientation data g.

Therefore, the orientation of the brightness measurement device 3 follows the visual-point position St of the viewer, and the viewer's feeling determination device 1 can automatically and accurately measure the visual-point position luminance Tt in real time. That is, after the content is viewed by the viewer and the visual-point position St is measured, it is unnecessary to display the content again and measure the visual-point position luminance Tt, so that it is possible to save time and effort to perform re-display of the content. In addition, the viewer's feeling determination device 1 can obtain the visual-point position luminance Tt with high accuracy, and as a result, it is possible to calculate the attention degrees P1t and P2t and the like with high accuracy.

Figure 27:
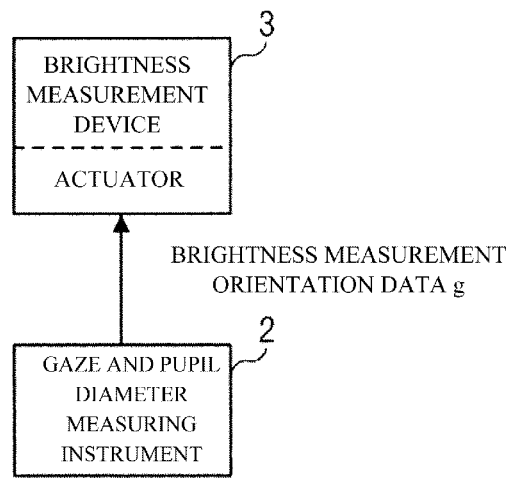
FIG. 27 is a block diagram for describing a second example of automatically measuring the visual-point position luminance Tt.

Next, a second example of automatically measuring the visual-point position luminance Tt will be described. The second example is an example in which the visual-point position luminance Tt is measured more real time than in the first example. FIG. 27 is a block diagram for describing a second example of automatically measuring the visual-point position luminance Tt.

In the second example, the viewer's feeling determination device 1 in the viewer's feeling determination system illustrated in FIG. 1 has the same components as those in FIG. 2. Similarly to the first example, the gaze and pupil diameter measuring instrument 2 measures the visual-point position St of the viewer with respect to content (with respect to a screen of the display 8) based on the visual image a and the eyeball movement image b, and measures a direction of the visual-point position St with the viewer's eye as the base point, thereby generating gaze direction data f.

The gaze and pupil diameter measuring instrument 2 generates the brightness measurement orientation data g by setting the gaze direction data f directly to the brightness measurement orientation data g. Then, the gaze and pupil diameter measuring instrument 2 transmits the brightness measurement orientation data g to the brightness measurement device 3.

Incidentally, the gaze and pupil diameter measuring instrument 2 may read correction data corresponding to the gaze direction data f from a memory unit (not illustrated) to correct the gaze direction data f based on the correction data and generate the brightness measurement orientation data g similarly to the first example. In this case, the gaze direction data f and the correction data corresponding to the gaze direction data f are stored in advance in the memory unit (not illustrated).

In this manner, the gaze and pupil diameter measuring instrument 2 generates the gaze direction data f based on the visual image a and the eyeball movement image b, generates the brightness measurement orientation data g based on the gaze direction data f, and transmits the brightness measurement orientation data g to the brightness measurement device 3 according to the second example of automatically measuring the visual-point position luminance Tt. As a result, the brightness measurement device 3 can change the orientation of the brightness measurement device 3 to the orientation of the visual-point position St based on the brightness measurement orientation data g directly received from the gaze and the pupil diameter measurement device 2.

Therefore, the orientation of the brightness measurement device 3 immediately follows the visual-point position St of the viewer, and the viewer's feeling determination device 1 can automatically and accurately measure the visual-point position luminance Tt in more real time as compared to the case of using the brightness measurement orientation data g from the viewer's feeling determination device 1. That is, after the content is viewed by the viewer and the visual-point position St is measured, it is unnecessary to display the content again and measure the visual-point position luminance Tt, so that it is possible to save time and effort to perform re-display of the content. In addition, the viewer's feeling determination device 1 can obtain the visual-point position luminance Tt with high accuracy, and as a result, it is possible to calculate the attention degrees P1t and P2t and the like with high accuracy.

As described above, the example in which the direction of luminance measurement performed by the brightness measurement device 3 is caused to follow the visual-point position St has been described in the viewer's feeling determination system illustrated in FIG. 1. The same description is also applied in the viewer's feeling determination system illustrated in FIG. 18. Hereinafter, a modification of the viewer's feeling determination system illustrated in FIG. 18 will be described.

Figure 28:
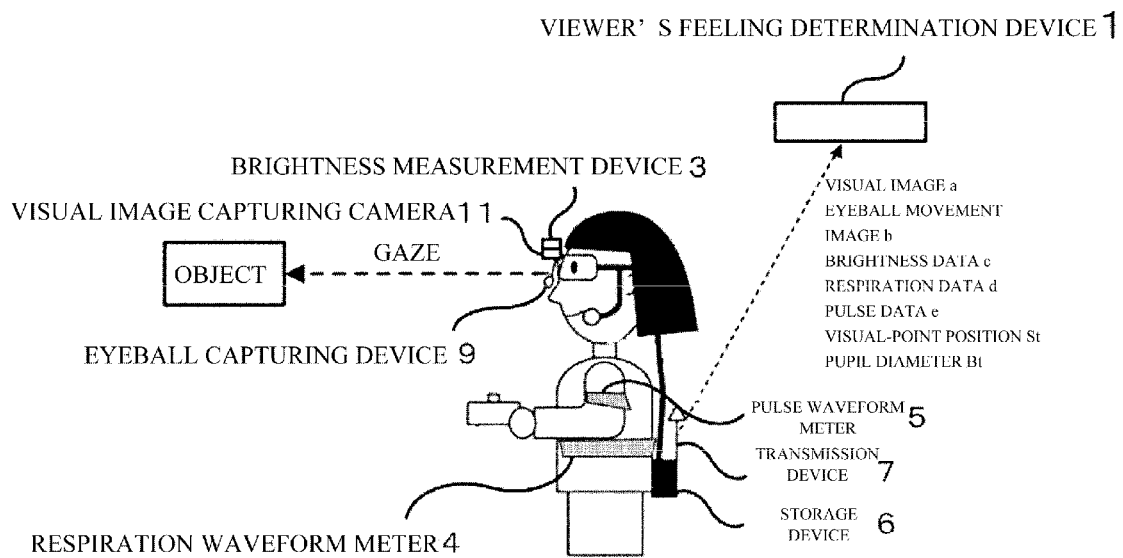
FIG. 28 is a schematic view illustrating a configuration example obtained by modifying the viewer's feeling determination system illustrated in FIG. 18.

FIG. 28 is a schematic view illustrating a configuration example obtained by modifying the viewer's feeling determination system illustrated in FIG. 18, that is, the example of automatically measuring the visual-point position luminance Tt in an open environment. This viewer's feeling determination system is configured to include the viewer's feeling determination device 1, the brightness measurement device 3, the respiration waveform meter 4, the pulse waveform meter 5, the storage device 6, the transmission device 7, an eyeball capturing device 9, and a visual image capturing camera 11.

The brightness measurement device 3 and the visual image capturing camera 11 are integrally configured so that the direction of luminance measurement performed by the brightness measurement device 3 follows the visual-point position St. Hereinafter, the brightness measurement device 3 and the visual image capturing camera 11 thus integrally configured will be referred to as a brightness measurement and visual image capturing device.

The brightness measurement and visual image capturing device acquires the visual image a captured by the visual image capturing camera 11 and receives input of the eyeball movement image b from the eyeball capturing device 9. Then, the brightness measurement and visual image capturing device measures the visual-point position St with respect to an object in the open environment based on the visual image a and the eyeball movement image b, measures a direction (gaze direction) of the visual-point position St with the viewer's eye as the base point, and generates the gaze direction data f. In addition, the brightness measurement and visual image capturing device obtains the pupil diameter Bt of the viewer based on the eyeball movement image b.

As described above, the brightness measurement and visual image capturing device generates the brightness measurement orientation data g based on the gaze direction data f, and changes the orientation of the brightness measurement device 3 to the orientation indicated by the brightness measurement orientation data g using the actuator provided in the brightness measurement device 3.

Figure 29:
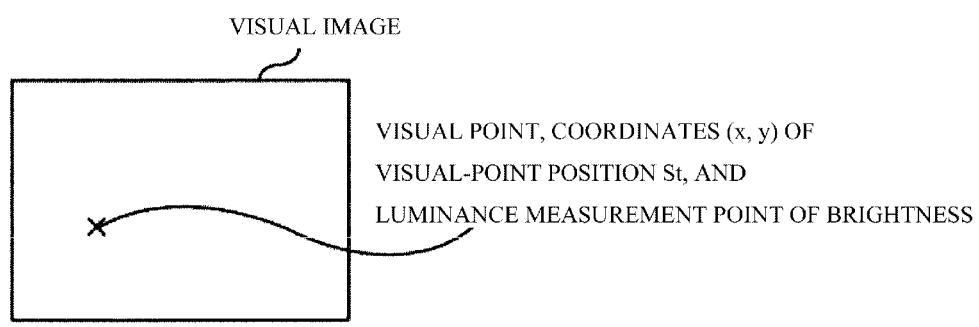

FIG. 29 is a view for describing the visual-point position St and the like inside the visual image a. As illustrated in FIG. 29, the orientation of the brightness measurement device 3 can be caused to be aligned a direction of coordinates (x, y) of the visual-point position St at a visual point inside the visual image a by the brightness measurement and visual image capturing device. Then, the brightness measurement and visual image capturing device can acquire the brightness data c of the visual-point position St.

The brightness measurement and visual image capturing device transmits the viewer image a, the eyeball movement image b, the brightness data c, the visual-point position St, and the pupil diameter Bt to the viewer's feeling determination device 1 via the transmission device 7.

In this manner, the brightness measurement device 3 of the brightness measurement and visual image capturing device can be directed toward the visual-point position St inside the visual image a using the actuator provided in the brightness measurement device 3, and it is possible to measure the luminance of the visual-point position St of the object. That is, the orientation of the brightness measurement device 3 immediately follows the visual-point position St of the object, and the viewer's feeling determination device 1 can automatically and accurately measure the visual-point position luminance Tt in real time.

For example, when a worker who is the viewer is performing an occupational safety work (for example, driving a car) that needs to immediately take action, the visual-point position luminance Tt can also be obtained in real time together with the pupil diameter Bt, the attention degrees P1$t$ and P2$t$, and the like. Therefore, the viewer's feeling determination device 1 can detect an inattentive (unwatched) state of the worker in real time, and instantly notify the worker of a warning or cause a brake operation.

In addition, the analysis unit 21 of the viewer's feeling determination device 1 illustrated in FIG. 2 measures the visual-point position St of the viewer based on the visual image a and the eyeball movement image b and measures the pupil diameter Bt of the viewer based on the eyeball movement image b in the above description. On the other hand, the gaze and pupil diameter measuring instrument 2 may have the function of obtaining the visual-point position St and the pupil diameter Bt. In this case, the gaze and pupil diameter measuring instrument 2 obtains the visual-point position St of the viewer based on the visual image a and the eyeball movement image b, and obtains the pupil diameter Bt of the viewer based on the eyeball movement image b.

Then, the reception unit 20 of the viewer's feeling determination device 1 also receives the visual-point position St and the pupil diameter Bt in addition to the visual image a and the eyeball movement image b from the gaze and pupil diameter measuring instrument 2, and the analysis unit 21 also receives the input of the visual-point position St and the pupil diameter Bt in addition to the visual image a and the like from the reception unit 20. The same description is also applied to the viewer's feeling determination device 1 illustrated in FIG. 18.

In addition, the brightness measurement device 3 causes the orientation of (the luminance meter provided in) the brightness measurement device 3 to be directed toward the visual-point position St using the actuator to measure the luminance of the visual-point position St in the above description. On the other hand, the brightness measurement device 3 may include an imaging unit 70 in which a plurality of luminance sensors (for example, photodiodes) are arranged, a visual-point position luminance measurement unit 71, and the like to correspond to the entire screen of a visual image of FIG. 29 (the screen of the display 8 in the example of FIG. 1).

Figure 30:
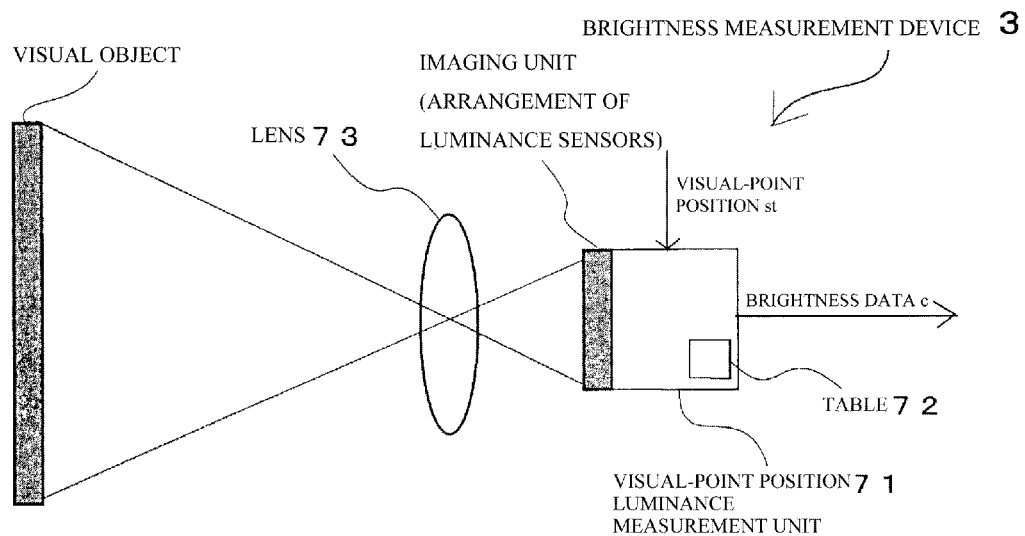
FIG. 30 is a view for describing a configuration and processing of a brightness measurement device.

FIG. 30 is a view for describing the configuration and processing of the brightness measurement device 3. The visual-point position luminance measurement unit 71 of the brightness measurement device 3 uses a table 72 in which the relationship between the luminance sensors and the visual-point positions St is defined to specify a luminance sensor at a position corresponding to the visual-point position St among the plurality of luminance sensors arranged in the imaging unit 70. Then, the visual-point position luminance measurement unit 71 stores the luminance measured by the luminance sensor via a lens 73 as the brightness data c in the storage device 6, and transmits the brightness data c to the viewer's feeling determination device 1 via the transmission device 7. The brightness data c measured in this manner is handled as the visual-point position luminance Tt, and the viewer's feeling determination device 1 can measure the visual-point position luminance Tt in real time.

Incidentally, a general computer can be used as a hardware configuration of the viewer's feeling determination device 1 according to the embodiment of the present invention. The viewer's feeling determination device 1 is configured using a computer that includes a CPU, a volatile storage medium such as a RAM, a nonvolatile storage medium such as a ROM, an interface, and the like. The respective functions of the reception unit 20, the analysis unit 21, the reference data measurement unit 22, the measurement unit 23, and the memory units 24 and 25 provided in the viewer's feeling determination device 1 are implemented by causing the CPU to execute programs describing these functions. In addition, these programs can also be distributed in the state of being stored in a storage medium such as a magnetic disk (a floppy (registered trademark) disks, a hard disk, or the like), an optical disk (a CD-ROM, a DVD, or the like), and a semiconductor memory, or can also transmitted and received via a network.

REFERENCE SIGNS LIST 1 viewer's feeling determination device
2 gaze and pupil diameter measuring instrument
3 brightness measurement device
4 respiration waveform meter
5 pulse waveform meter
6 storage device 7 transmission device
8 display
9 eyeball capturing device
10 visual scene capturing device
11 visual image capturing camera
20 reception unit
21 analysis unit
22 reference data measurement unit
23 measurement unit
24, 25 memory unit
26 transmission unit
30 reference brightness/darkness response measuring unit
31 reference respiration response measuring unit
32 reference pulse response measuring unit
33 reference pupil diameter and others specifying unit
34 attention pupil diameter and others calculating unit
35 attention degree calculating unit
40, 43, 47 moving average time setting section
41, 44, 48 moving-averaged pupil diameter calculating section
42, 46, 51 attention pupil diameter and others calculating section.
45, 50 respiration response eliminating section
49 pulse response eliminating section
60 reference brightness/darkness response table
61 reference respiration response table
62 reference pulse response table
70 capturing unit
71 visual-point position luminance measurement unit
72 table
73 lens

The invention claimed is:

1. A viewer's feeling determination device that determines a feeling of a viewer based on a pupil diameter of the viewer who views content displayed on a display, the viewer's feeling determination device comprising:
  a memory unit that, when a predetermined reference brightness/darkness screen is displayed on a first screen and brightness of the first screen and brightness of a visual-point position when a visual point of the viewer is aligned to a predetermined position on the first screen are changed, stores reference data relating to the pupil diameter of the viewer based on a pupil diameter of the viewer measured for each of combinations of the brightness of the first screen and the brightness of the visual-point position in the reference brightness/darkness screen; and
  a measurement unit that measures a pupil diameter of the viewer when the content is displayed on the display to obtain an actually-measured pupil diameter, specifies the reference data corresponding to brightness of the display on which the content is displayed and brightness of a visual-point position in the display on which the content is displayed based on the reference data stored in the memory unit, and corrects the actually-measured pupil diameter based on the actually-measured pupil diameter and the specified reference data to obtain a corrected pupil diameter, wherein
  the reference data is measured by a reference data measurement unit, the reference data measurement unit comprises
    a reference brightness/darkness response measuring unit that moving-averages the pupil diameter over a time interval to obtain a moving-averaged pupil diameter for each of the combinations of the brightness of the first screen and the brightness of the visual-point position in the reference brightness/darkness screen, averages the moving-averaged pupil diameter based on a time for which the reference brightness/darkness screen is displayed to obtain a reference pupil diameter, and generates a reference brightness/darkness response table including the reference pupil diameter for each of the combinations of the brightness of the first screen and the brightness of the visual-point position in the reference brightness/darkness screen, and
  the measurement unit comprises:
    a reference pupil diameter and others specifying unit that specifies the reference pupil diameter using brightness of the screen and position from the reference brightness/darkness response table, which corresponds to the brightness of the display on which the content is displayed and the brightness of the visual-point position in the display on which the content is displayed, based on the reference brightness/darkness response table generated by the reference brightness/darkness response measuring unit; and
    a unit that sets a predetermined time interval equal of the two respiration times or more, moving-averages the pupil diameter over the predetermined time interval to obtain a moving-averaged pupil diameter and define the moving-averaged pupil diameter as an attention pupil diameter, and subtracts the reference pupil diameter specified by the reference pupil diameter and others specifying unit from the moving-averaged pupil diameter to obtain a pupil diameter corresponding to attention.

2. The viewer's feeling determination device according to claim 1, further comprising
  an analysis unit that measures respiration state data including timings of an inhalation start point and an exhalation start point in the viewer's respiration,
  wherein the reference data measurement unit further comprises
  a reference respiration response measuring unit that sets a predetermined time interval of two pulse times or more and less than two respiration times with to respiration cycle of the viewer as one respiration time and a pulse cycle of the viewer as one pulse time, moving-averages the pupil diameter over the time interval for each of the combinations of the brightness of the first screen and the brightness of the visual-point position in the reference brightness/darkness screen to obtain a moving-averaged pupil diameter, averages the moving-averaged pupil diameter based on a time for which the reference brightness/darkness screen is displayed to obtain an average value, subtracts the average value from the moving-averaged pupil diameter to obtain a pupil diameter influenced only by the respiration as a subtraction result, and extracts a respiration pupil diameter in a time of one respiration cycle including the inhalation start point and the exhalation start point from a temporal change of the pupil diameter influenced only by the respiration using the respiration state data measured by the analysis unit to generate a reference respiration response table formed of the respiration pupil diameter for each of the combinations of the brightness of the first screen and the brightness of the visual-point position in the reference brightness/darkness screen,
  the reference pupil diameter and others specifying unit of the measurement unit specifies the reference pupil diameter and further specifies the respiration pupil diameter corresponding to the brightness of the display on which the content is displayed and the brightness of the visual-point position in the display on which the content is displayed based on the reference respiration response table generated by the reference brightness/darkness response measuring unit, and an attention pupil diameter and others calculating unit of the measurement unit sets the predetermined time interval of two pulse times or more and less than two respiration times, moving-averages the pupil diameter over the time interval being set by the attention pupil diameter and others calculating unit to obtain the moving-averaged pupil diameter, subtracts the respiration pupil diameter specified by the reference pupil diameter and others specifying unit from the moving-averaged pupil diameter to obtain the attention pupil diameter, and further subtracts the reference pupil diameter specified by the reference pupil diameter and others specifying unit from a result of the subtraction to obtain the pupil diameter corresponding to attention.

3. The viewer's feeling determination device according to claim 2, wherein the analysis unit measures pulse state data including a timing of a pulse start point in the viewer's pulse in addition to the respiration state data, the reference data measurement unit further comprises a reference pulse response measuring unit that sets a predetermined time interval of two pulse times or more and less than two respiration times with the respiration cycle of the viewer as one respiration time and the pulse cycle of the viewer as one pulse time, moving-averages the pupil diameter over the time interval to obtain the moving-averaged pupil diameter, subtracts the moving-averaged pupil diameter from the pupil diameter to obtain a pupil diameter influenced only by the pulse as a subtraction result, and extracts a pulse pupil diameter in a time of one pulse cycle including the pulse start point from a temporal change of the pupil diameter influenced only by the pulse using the pulse state data measured by the analysis unit to generate a reference pulse response table formed of the pulse pupil diameter for each of the combinations of the brightness of the first screen and the brightness of the visual-point position in the reference brightness/darkness screen, the reference pupil diameter and others specifying unit of the measurement unit specifies the reference pupil diameter and the respiration pupil diameter and further specifies the pulse pupil diameter corresponding to the brightness of the display on which the content is displayed and the brightness of the visual-point position in the display on which the content is displayed based on the reference pulse response table generated by the reference brightness/darkness response measuring unit, and the attention pupil diameter and others calculating unit of the measurement unit subtracts the pulse pupil diameter and the respiration pupil diameter specified by the reference pupil diameter and others specifying unit from the pupil diameter to obtain an attention pupil diameter, and further subtracts the reference pupil diameter specified by the reference pupil diameter and others specifying unit from a result of the subtraction to obtain the pupil diameter corresponding to attention.

4. The viewer's feeling determination device according to claim 3, wherein the measurement unit further comprises an attention degree calculating unit that calculates a ratio between the reference pupil diameter specified by the reference pupil diameter and others specifying unit and the attention pupil diameter obtained by the attention pupil diameter and others calculating unit to obtain a first attention degree, or calculates a ratio between the reference pupil diameter specified by the reference pupil diameter and others specifying unit and the pupil diameter corresponding to attention obtained by the attention pupil diameter and others calculating unit to obtain a second attention degree.

5. The viewer's feeling determination device according to claim 4, wherein when a plurality of division areas obtained by dividing a screen of the display are set and there are a plurality of the viewers, the measurement unit obtains an attention degree for each of the plurality of the viewers with respect to the content by obtaining the first attention degree with respect to the content displayed on the display as a first content attention degree for each of the plurality of the viewers, summing the first content attention degrees for the plurality of the viewers to obtain a first total result, and dividing the first total result by total number of the plurality of the viewers, obtains a distribution of attention degrees for each of the division areas with respect to the content by obtaining the first attention degree for each of the division areas as a first area attention degree for each of the plurality of the viewers, summing the first area attention degrees for the plurality of the viewers to obtain a second total result, and dividing the second total result by the first total result, and obtains a distribution of attention degrees for each of the division areas per unit time with respect to the content by integrating the distribution of attention degrees for each of the division areas with respect to the content based on a predetermined time period to obtain a total distribution of attention degrees for each of the division areas, and dividing the total distribution of the attention degrees for each of the division areas by the predetermined time period.

6. The viewer's feeling determination device according to claim 4, wherein when a screen of a questionnaire including a question field and a plurality of answer fields is displayed on the display, the measurement unit obtains each field attention degree for each of the question fields and the plurality of answer fields by integrating the first attention degree for each of the question fields and the plurality of answer fields based on a predetermined time period, obtains a first total result by summing the field attention degrees, respectively, for the question field and the plurality of answer fields and obtains a second total result by summing the field attention degrees, respectively, for the plurality of answer fields, obtains an answering confidence ratio for each of the plurality of answer fields by dividing each of the field attention degrees for each of the plurality of answer fields by the second total result, and obtains a level of an attention degree for the questionnaire by dividing the first total result by the predetermined time period.

7. The viewer's feeling determination device according to claim 1, wherein the pupil diameter of the viewer, which is obtained based on the reference data, is measured after one second or more or one minute or less for each change of a predetermined reference brightness/darkness screen of the first screen, after a lapse of 40 seconds or more or ten minutes or less since the predetermined reference brightness/darkness screen of the first screen is first displayed for the viewer.

* * * * *